US007982021B2

(12) United States Patent
Zhang et al.

(10) Patent No.: US 7,982,021 B2
(45) Date of Patent: Jul. 19, 2011

(54) NUCLEIC ACID MOLECULES ENCODING EMISSION RATIOMETRIC INDICATORS OF PHOSPHOINOSITIDES

(75) Inventors: Jin Zhang, Baltimore, MD (US); Bharath Ananthanarayanan, Scotch Plains, NJ (US)

(73) Assignee: The Johns Hopkins University, Baltimore, MD (US)

( * ) Notice: Subject to any disclaimer, the term of this patent is extended or adjusted under 35 U.S.C. 154(b) by 601 days.

(21) Appl. No.: 11/826,519

(22) Filed: Jul. 16, 2007

(65) Prior Publication Data

US 2008/0096224 A1 Apr. 24, 2008

Related U.S. Application Data

(60) Provisional application No. 60/830,811, filed on Jul. 14, 2006.

(51) Int. Cl.
C07H 21/02 (2006.01)
C08H 1/00 (2006.01)
(52) U.S. Cl. ..................... 536/23.1; 435/69.7
(58) Field of Classification Search ........................ None
See application file for complete search history.

(56) References Cited

U.S. PATENT DOCUMENTS

| 2002/0137115 | A1 | 9/2002 | Umezawa et al. |
| 2003/0186229 | A1 | 10/2003 | Tsien et al. |
| 2005/0026234 | A1 | 2/2005 | Violin et al. |
| 2005/0054573 | A1 | 3/2005 | Werner et al. |
| 2007/0111270 | A1 | 5/2007 | Zhang et al. |

FOREIGN PATENT DOCUMENTS

WO    WO 2007/050734    5/2007

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Ananthanarayanan et al, Signal propagation from membrane messengers to nuclear effectors revealed by reporters of phosphoinositide dynamics and Akt activity. Proc Natl Acad Sci U S A. Oct. 18, 2005;102(42):15081-6. Epub Oct. 7, 2005.*
van der Wal et al, Monitoring agonist-induced phospholipase C activation in live cells by fluorescence resonance energy transfer. J Biol Chem. May 4, 2001;276(18):15337-44. Epub Jan. 10, 2001.*
Andreotti Regulatory intramolecular association in a tyrosine kinase of the Tec family. Nature. Jan. 2, 1997;385(6611):93-7.*
Matsu-ura et al, Cytosolic inositol 1,4,5-trisphosphate dynamics during intracellular calcium oscillations in living cells. J Cell Biol. Jun. 5, 2006;173(5):755-65.*
Balla, T. & Várnai, P. (2002), "Visualizing Cellular Phosphoinositide Pools with GFP-Fused Protein-Modules," *Sci. STKE.*, L3.

Burks et al., "IRS pleckstrin homology domains bind to acidic motifs in proteins," *J. Biol. Chem.* 273, 31061-67, Nov. 20, 1998.
Cicchetti et al., "A Ratiometric Expressible FRET Sensor for Phosphoinositides Displays a Signal Change in Highly Dynamic Membrane Structures in Fibroblasts," *Biochemistry* 43, 1939-49, 2004.
Gray et al., "The pleckstrin homology domains of protein kinase B and GRP1 (general receptor for phosphoinositides-1) are sensitive and selective probes for the cellular detection of phosphatidylinositol 3,4-bisphosphate and/or phosphatidylinositol 3,4,5-triphosphate in vivo," *Biochem. J.* 344, 929-36, 1999.
Insall, "Protein conformation: through a lens, darkly," *Biochem. J.* 372, Epub 10.1042/BJ20030358COM), May 8, 2003.
Luo et al., "Targeting the P13K-Akt pathway in human cancer: Rationale and promise," *Cancer Cell.* 4, 257-262, 2003.
Miyawaki, "Visualization of the spatial and temporal dynamics of intracellular signaling," *Dev Cell.* Mar. 2003;4(3):295-305.
Nagai et al., "Expanded dynamic range of fluorescent indicators for $Ca^{2+}$ by circularly permuted yellow fluorescent proteins," *Proc. Natl. Acad. Sci. USA* 101, 10554-59, Jul. 20, 2004.
Neri et al., "The nuclear phosphoinositide 3-kinase/ AKT pathway : a new second messenger system," *Biochim. Biophys. Acta* 1584, 73-80, 2002.
Nishi et al., "Visualization of Glucocorticoid Receptor and Mineralocorticoid receptor Interactions in Living Cells with GFP-Based Fluorescence Resonance Energy Transfer," *J. Neurosci.* 24, 4918-27, May 26, 2004.
Oatey et al., "Confocal imaging of the subcellular distribution of phosphatidylinositol 3, 4, 5-triphosphate in insulin- and PDGE-stimulated 3T3-L1 adipocytes," *Biochem. J.* 344, 511-18, 1999.
Sato et al., "Production of PtdInsP3 at endomembranes is triggered by receptor endocytosis," *Nature Cell Biology* 5, 1016-1022, Epub Oct. 5, 2003.
Stauffer et al., "Receptor-induced transient reduction in plasma membrane PtdIns(4,5)P2 concentration monitored in living cells," *Curr Biol.* 8(6):343-46, Mar. 12, 1998. Toker, "Phosphoinositides and signal transduction," *Cell Mol. Life Sci.* 59, 761-79, 2002.
Várnai & Balla, "Visualization of Phosphoinositides That Bind Pleckstrin Homology Domains: Calcium- and Agonist-induced Dynamic Changes and Relationship to Myo[$^3$H]inositol-labeled Phosphoinositide Pools," *J. Cell Biol.* 143, 501-510, Oct. 19, 1998.
Zhang et al., "Genetically encoded reporters of protein kinase A activity reveal impact of substrate tethering," *Proc. Natl. Acad. Sci. U.S.A.* 98, 14997-15002, 2001.
Zhang et al., "Creating new fluorescent probes for cell biology," Nat Rev Mol Cell Biol. 3(12):906-18, Dec. 2002.

\* cited by examiner

*Primary Examiner* — Sheridan Swope
(74) *Attorney, Agent, or Firm* — Banner & Witcoff, Ltd.

(57) ABSTRACT

Nucleic acid molecules encoding emission ratiometric indicators of phosphoinositides, which comprise a fusion protein comprising a pleckstrin homology (PH) domain of Akt (also known as protein kinase B) and a "pseudoligand" containing acidic amino acid residues, which is sandwiched between resonance energy transfer (RET) pairs, such as cyan and yellow mutants of GFP (a FRET pair). The nucleic acid molecules can be used, for example, to produce the indicators which can be used, inter alia, to monitor spatiotemporal dynamics of phosphoinositides and in high throughput assays for inhibitors of PI3K, including drug screening assays.

4 Claims, 8 Drawing Sheets
(8 of 8 Drawing Sheet(s) Filed in Color)

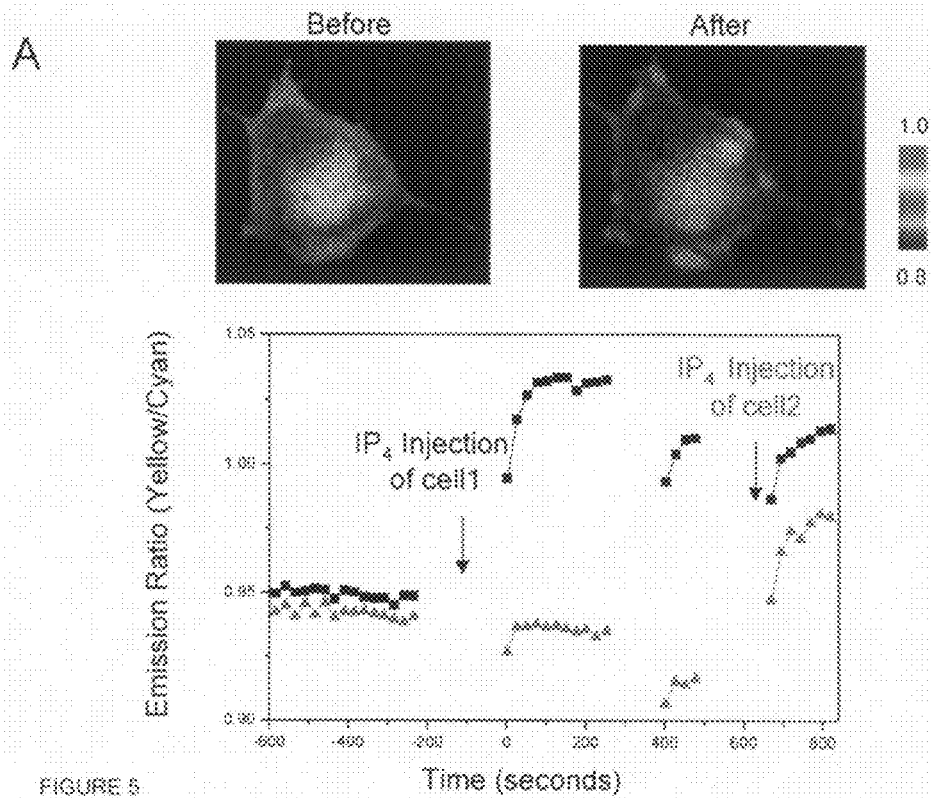
FIGURE 5
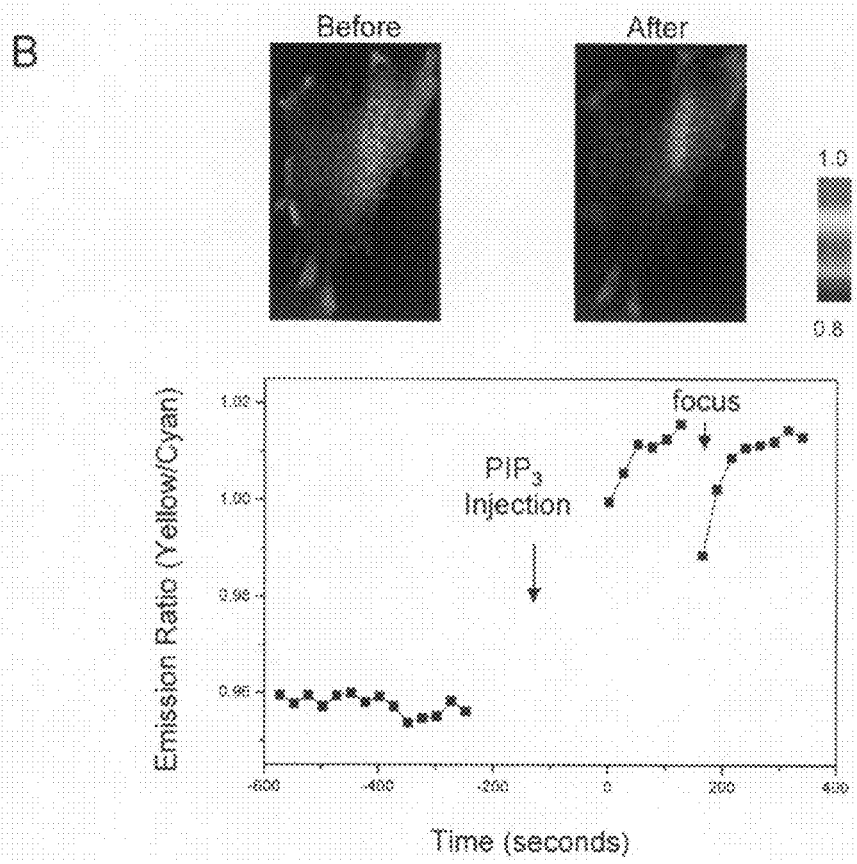

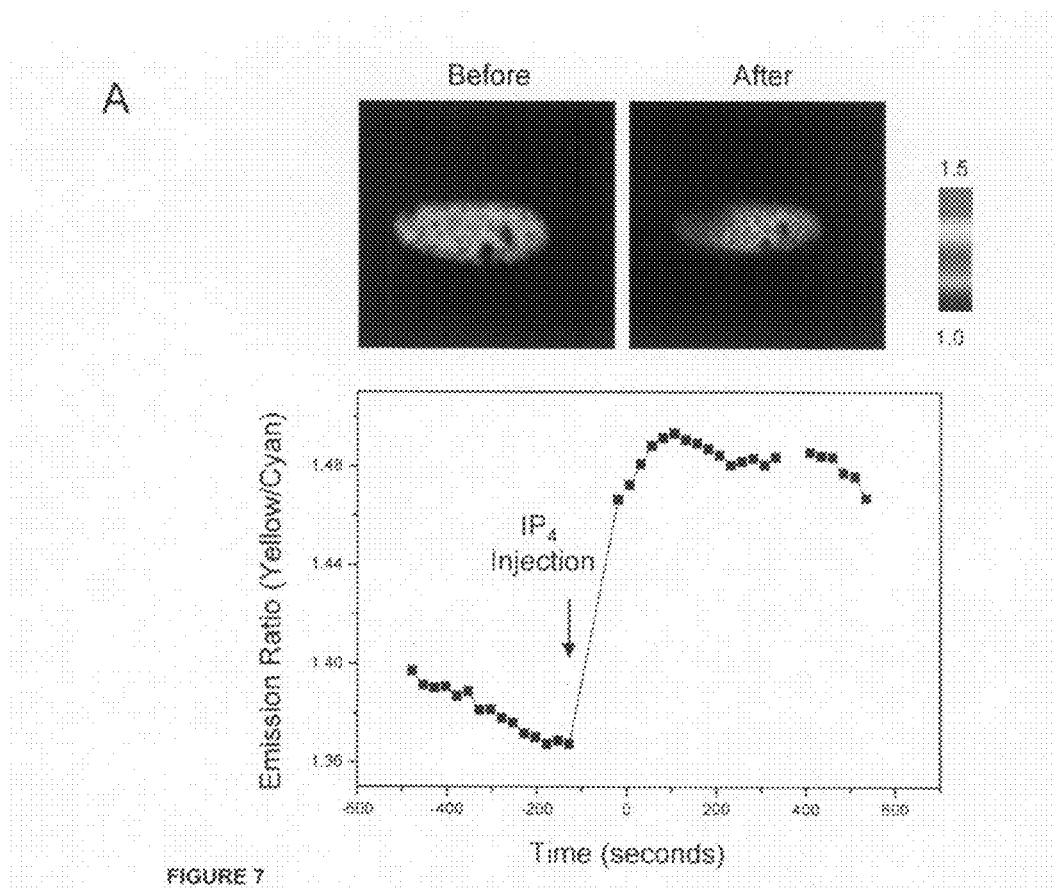
FIGURE 7
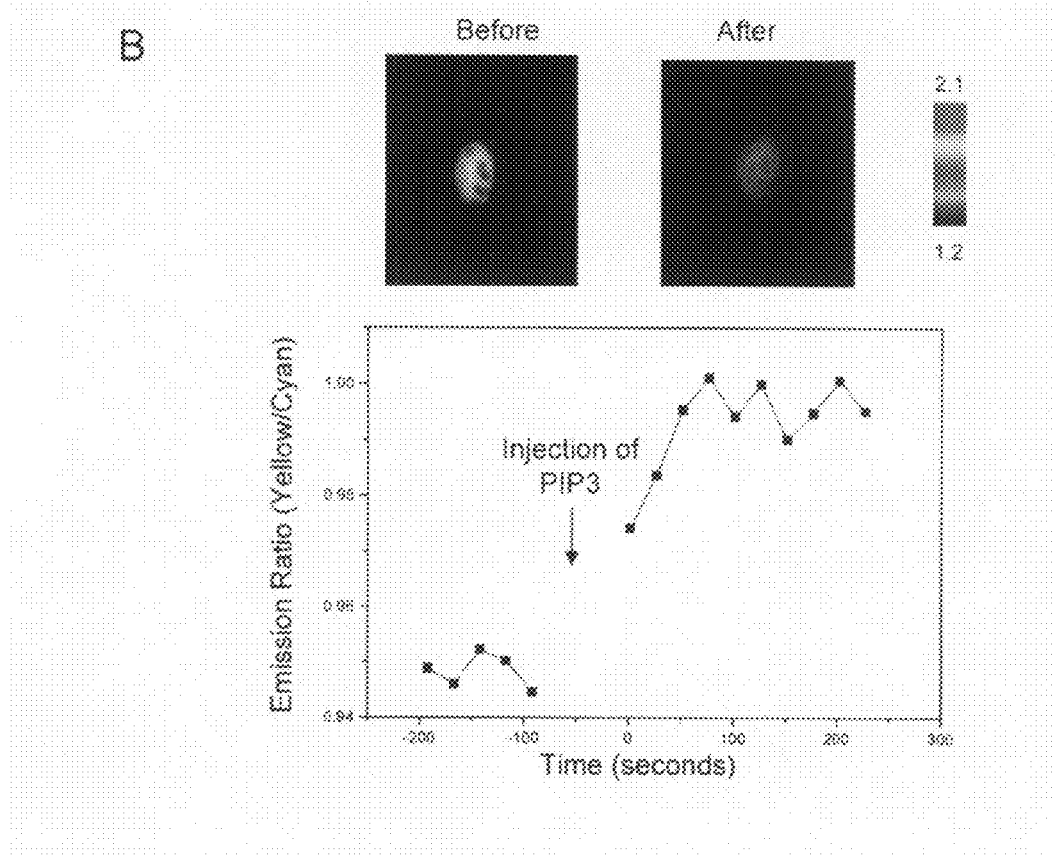

| Protein | Lipid | $K_d$ (M) Dissociation constant |
|---|---|---|
| PH-pseudoL-YFP | PI(3,4)P$_2$ | $(6.22 \pm 1.4) \times 10^{-9}$ |
| | PI(3,4,5)P$_3$ | $(6.24 \pm 2.9) \times 10^{-9}$ |
| | PI(4,5)P$_2$ | no appreciable specific binding |
| PH-pseudoL-YFP -CAAX | PI(3,4)P$_2$ | $(13.72 \pm 5.7) \times 10^{-9}$ |
| | PI(3,4,5)P$_3$ | $(19.45 \pm 4.8) \times 10^{-9}$ |
| | PI(4,5)P$_2$ | no appreciable specific binding |
| PH-pseudoL-YFP -NLS | PI(3,4)P$_2$ | $(9.01 \pm 3.8) \times 10^{-9}$ |
| | PI(3,4,5)P$_3$ | $(15.62 \pm 6.2) \times 10^{-9}$ |
| | PI(4,5)P$_2$ | no appreciable specific binding |

NUCLEIC ACID MOLECULES ENCODING EMISSION RATIOMETRIC INDICATORS OF PHOSPHOINOSITIDES

This application claims the benefit of application Ser. No. 60/830,811 filed Jul. 14, 2006, which is incorporated herein by reference in its entirety.

This application incorporates by reference a 25.9 kb text file created on Jan. 12, 2010 and named "SN11826519_sequencelisting.txt," which is the sequence listing for this application.

FIELD OF THE INVENTION

The invention relates to the monitoring of phosphoinositides in living mammalian cells.

BACKGROUND OF THE INVENTION

Ligand activation of the receptors in the plasma membrane initiates cell signaling which propagates into various intracellular compartments through multi-step processes that depend on cellular second messengers. It has been shown that these short lived small molecules not only amplify the signal in the relay but also confer specificity by their temporal and spatial distribution in the cell.

Although a relatively minor component of cellular membranes, phosphoinositides (PIs) are emerging to be a crucial component and a diverse family of lipid second messengers (1). The family's diversity stems from the existence of multi-phosphorylated states at the D-3, -4 and -5 positions, yielding seven distinct signaling molecules identified to date (2). In particular, phosphatidylinositol 3-kinase (PI3K) synthesizes four species of D-3 phosphorylated inositides, namely phosphatidylinositol 3,4,5 triphosphate ($PIP_3$; also known as "PI$(3,4,5)P_3$"), $PI(3,4)P_2$, $PI(3,5)P_2$ and $PI(3)P$ (3). On the other hand, they are dephosphorylated by the 3'-phosphatase called phosphatase and tensin homologue deleted on chromosome ten (PTEN) and some by 5'-phosphatases (4, 5). $PIP_3$ and $PI(3,4)P_2$ are responsible for the recruitment of the serine/threonine kinase Akt, also known as and referred to herein as protein kinase B (PKB), to the plasma membrane where phosphorylation at two sites, T308 and S473 (in Akt1), fully activates the kinase (6, 7).

Upon activation Akt plays important roles in various cellular processes such as proliferation, differentiation, survival, and tumorigenesis (8). For example, activation of Akt by insulin or growth factors is prevented if the cells are preincubated with inhibitors of PI 3-kinase, the best known being Wortmannin or LY 294002, or by overexpression of a dominant negative mutant of PI 3-kinase (44). Further, mutation of the tyrosine residues in the PDGF receptor that when phosphorylated bind to PI 3-kinase also prevent the activation of $PKB_\alpha$, an isoform of PKB. Recent reports have shown the PKB is itself activated by another kinase also downstream of PIP3 (45). This kinase, termed PKB kinase, or phosphatidylinositide (PtdIns) 3-kinase (PDK1), requires PIP3 for activation (46).

Akt also is involved in regulating cell growth. It has been implicated in certain human cancers; for instance, it is known to be amplified in a percentage of ovarian carcinomas, breast carcinomas, and pancreatic carcinomas (47; 48). The amplification of the enzyme affords tumor cells a mechanism to circumvent apoptosis. Drugs that inhibit PKB activity are useful for treating diseases involving inappropriate cell growth, including cancer.

Due to the involvement of these PIs in such diverse functions, a cell must precisely control their spatial and temporal dynamics to avoid abnormalities, yet there are no reliable methods available for measuring $PIP_3$, $PI(3,4)P_2$ dynamics within subcellular compartments with high spatiotemporal resolution. Previously employed indicators cause artifacts due to cell movements and additionally cannot be targeted to subcellular locations. Biochemical methods of radiolabeling and cell fractionation measure total PI levels and have poor spatial and temporal resolution, and use of specific antibodies (31) to immunodetect PIs in fixed cells provides only snapshots at different time points. For dynamic monitoring of the lipid molecules, live-cell imaging using PH domains fused with fluorescent proteins (10-13, 32, 33) has been widely used, however their dependency on translocation limits their abilities to examine different pools of PIs.

There are ratiometric sensors for monitoring PI dynamics. On such sensor, termed "fllip" (34), employs a PH domain of GRP1 and required membrane anchoring to facilitate a $PIP_3$ binding induced conformational change via rotation of rigid linkers around a diglycine hinge engineered within the construct, which limits the targetability of the reporter and generalizability of the design. Another ratiometric sensor, termed "CAY," is based on a peptide from *Listeria* protein ActA that undergoes a random coil to helix transition upon lipid binding (35). CAY is a sensor for polyphosphorylated PIs showing some preference for $PIP_3$ in cells.

There is a need in the art for sensitive, targetable indicators that would permit direct measurement and assessment of specific signaling of 3'-phosphoinositides.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A, cartoon depicting the conformational change upon PI binding, yielding a FRET response. FIG. 1B, domain structure of the construct showing the restriction sites linking individual components. These are a SphI site (GCATGC), shown in the sequence GCATGCAT; a PstI site (CTGCAG), shown in the sequence TCTGCAGGCGGTAGC (SEQ ID NO:22, encoding SEQ ID NO:23); and a Sac I site (GAGCTC), shown in the sequence GGCGGCAGCGAGCTC (SEQ ID NO:24, encoding SEQ ID NO:25). FIG. 1C, anti-GFP Western blot of InPAkt expressed in HEK293 cells indicating the right size of the reporter. FIG. 1D, FRET response of InPAkt expressed in NIH3T3 cells. Yellow fluorescence images show membrane translocation of InPAkt upon PDGF stimulation. Pseudocolor images indicate the emission ratio change at various time points after PDGF stimulation. FIG. 1E, representative emission ratio time courses of InPAkt (n=9) and the PH domain mutant R23A/R25A (n=2), both stimulated with 50 ng/ml PDGF. InPAkt showed a response of 25.4±3.7% [average±std] (n=9). FIG. 1F, representative emission ratio time course from two independent experiments showing that the response of InPAkt is PI3K specific. NIH3T3 cells were pretreated with 20 µM of PI3K inhibitor LY294002, followed by stimulation with 50 ng/ml PDGF, gentle washing, and treatment with PDGF again. FIG. 1G, representative emission ratio time course shows the reversibility of the reporter. NIH3T3 cells expressing InPAkt were stimulated with PDGF, followed by treatment with 20 µM of LY294002 (n=5).

FIG. 2A, representative time courses of InPAkt responses in cells stimulated by 50 ng/ml PDGF (blue), 50 nM IGF-1 (yellow), 100 ng/ml insulin (green) (n=3). FIG. 2B, representative emission ratio time courses showing the FRET response of a NIH3T3 cell expressing InPAkt sequentially stimulated by insulin, IGF-1 and PDGF (n=3). FIG. 2C, pseudocolor images showing InPAkt responses with sequential stimulation by insulin, IGF-1 and PDGF.

FIG. 3A, domain structure of the fusion constructs. FIG. 3B, localization of plasma membrane targeted InPAkt (pm InPAkt) is shown in the fluorescence image (YFP). Pseudocolor images show colocalization of nuclear targeted reporter (NLS InPAkt) with a cell-permeable DNA dye, Hoechst 3342. FIG. 3C, representative emission ratio time course from four independent experiments showing the response of plasma membrane targeted InPAkt stimulated with 50 ng/ml PDGF (9.25±0.4%), followed by addition of 20 µM LY294002. FIG. 3D, representative emission ratio time course from 3 different trials for NLS InPAkt in NIH3T3 cells stimulated with PDGF.

FIG. 4A, domain structure of NLS BKAR. FIG. 4B, pseudocolor images show colocalization of NLS BKAR with Hoechst 3342. FIG. 4C, cellular distribution of the two reporters in a HEK293 cell. FIG. 4D, representative emission ratio time courses from four different experiments for pm InPAkt and NLS BKAR in the same cell stimulated with 50 nM IGF-1.

FIGS. 5A-B. Responses of InPAkt indicator for phosphoinositides based on Akt, upon microinjection of IP4 and PI(3,4,5)P$_3$. FIG. 5A, Microinjection of IP4 into REF-52 cells expressing InPAkt. Pseudocolor images and emission ratio time courses show the change in the yellow-to-cyan emission ratio of InPAkt upon 1 mM IP4 microinjection. IP4 (AG Scientific) was dissolved in water to a final concentration of 1 mM, and this solution was used to load the microinjection tip. Shown in the graph are the responses of two individual cells imaged simultaneously but injected at two different time points (cell 1 in black and cell 2 in red). InPAkt showed 6.6+0.64% (n=5) increase in yellow/cyan emission ratio upon IP4 injection. REF-52 cells were used for ease of microinjection, particularly nuclear injection. FIG. 5B, microinjection of PI(3,4,5)P$_3$ into REF-52 cells expressing InPAkt. Pseudocolor images and emission ratio time courses show the FRET response of the reporter upon 5 mM dioctanoyl PI(3,4,5)P$_3$ microinjection. Dioctanoyl PI(3,4,5)P$_3$ (Echelon Biosciences) was dissolved in water, and solutions with final concentrations of 1-5 mM were loaded in the microinjection tip. Higher concentrations of PIP3 could not be used for microinjection experiments because of aggregation of the lipid thus clogging of the tip. InPAkt showed 4.1+0.40% (n=3) increases in yellow-to-cyan emission ratio upon PIP3 injection. Control experiments injecting water or buffers showed no change in the emission ratios. In some microinjection experiments, rhodamine B dextran (MW 10,000) was mixed with phosphoinositides, and the presence of red fluorescence in the cells after microinjection indicated successful injection.

FIGS. 7A-B. Responses of nuclear-targeted InPAkt upon microinjection of IP4 and PI(3,4,5)P$_3$. FIG. 7A, microinjection of IP4 into REF-52 cells expressing nuclear localization signal (NLS) InPAkt. Pseudocolor images and representative emission ratio time courses show the response of the nuclear-localized InPAkt (NLS InPAkt) upon nuclear injection of 1 mM IP4 (from AG Scientific). NLS InPAkt showed 9.1+0.42% (n=2) increases in yellow/cyan emission ratio upon IP4 injection. FIG. 7B, microinjection of PI(3,4,5)P$_3$ into REF-52 cells expressing NLS InPAkt. Pseudocolor images and representative emission ratio time courses show the response of NLS InPAkt upon nuclear injection of 5 mM dioctanoyl PI(3,4,5)P$_3$ (Echelon Biosciences). NLS InPAkt showed 5.4+2.2% (n=3) increases in yellow/cyan emission ratio upon PI(3,4,5)P$_3$ injection.

FIG. 8A, domain structure of PH Akt fusion constructs containing pseudoligand and the targeting sequences. All of the constructs were cloned into pRSET B bacterial expression vector with a N-terminal His6-tag. Proteins were purified by using Ni-NTA affinity chromatography (Qiagen) according to the manufacturer's protocol. The purified proteins were further dialyzed in 20 mM Tris.HCl buffer (pH 7.4) containing 0.16 M KCl. The purity of all of the proteins was checked by SDS protein gel electrophoresis. Concentrations of the proteins were determined by using the BCA assay. FIG. 8B, representative sensograms obtained from Biacore 2000 surface plasmon resonance. All of the four flow channels of the Pioneer L1 sensor chip were coated with large unilamellar vesicles containing four different lipid mixtures. Vesicles containing phospholipid compositions of mainly 70% of dioleoyl phosphatidylcholine (PC) and 30% diacyl phosphatidyl serine (PS) from porcine brain (Avanti Polar lipids) were made with additional 3% of the three different dipalmitoyl phosphatidylinositol ligands, namely PI(4,5)P$_2$, PI(3,4)P$_2$, and PI(3,4,5)P$_3$ (Echelon Biosciences). Large unilamellar vesicles were made by using an extruder in buffer containing 20 mM Tris.HCl (pH 7.4) and 0.16 M KCl. Experiments were performed at 25° C. After each injection, the immobilized vesicle surface on all of the flow channels was regenerated by using 10 ml of 50 mM NaOH for subsequent measurements. For data acquisition, four or more different concentrations of the protein were used. (Each sensogram shown in this figure has been normalized to zero to facilitate comparison between the responses of different lipid surfaces.) FIG. 8C, dissociation constants for PH Akt domain fusion constructs. Dissociation constants in the table represent the mean and standard deviation from four different measurements. All measurements were performed in buffer containing 20 mM Tris.HCl (pH 7.4) and 0.16 M KCl. Data were analyzed by using BIAEVALUATION 3.2 software (BIACOR®). Surface immobilized with vesicles containing PC:PS but no phosphatidylinositol was used as a control surface for background subtraction to eliminate any refractive index changes due to injections or buffer changes. Binding parameters for the PH domain constructs for PI(4,5)P$_2$ could not be evaluated in that no discernable difference was detected between binding to the PI(4,5)P$_2$ containing lipid surface and the control surface containing no phosphoinositides.

DETAILED DESCRIPTION OF THE INVENTION

Figure 1:
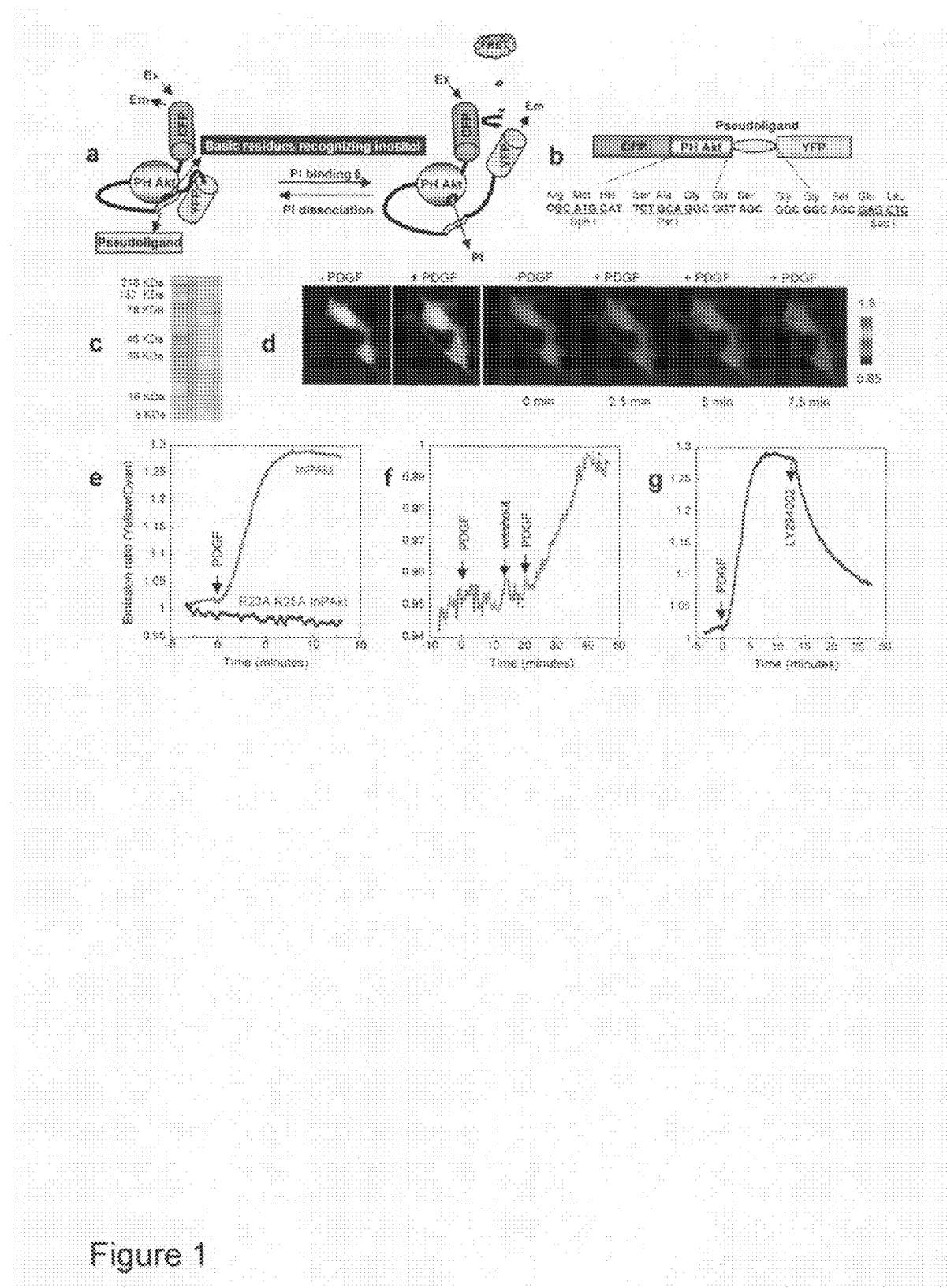
FIGS. 1A-G. Development of InPAkt.

The invention provides targetable phosphoinositide (PI) indicators. PI indicators of the invention have some unique advantages over previous methods for assessing phosphoinositide dynamics inside cells. They offer dual readout of RET change and translocation in their untargeted forms. The conformational change does not rely on any membrane anchoring, which provides the flexibility of targeting the reporters to different subcellular regions or tethering them to signaling components to track specific pools of PIs. They do not require large amounts of cells or tissue, provides high spatial and temporal resolution and eliminates artifacts caused by cell shape changes. In addition, they can be targeted to different subcellular sites or fused to signaling components and have the flexibility of monitoring specific pools of PIs and measuring PI changes within various subcellular compartments.

PI indicators of the invention are useful, inter alia, in high throughput assays for inhibitors of PI3K, including drug screening assays, and for diagnostic analysis of potential cancerous tissues. Furthermore, it may offer a generalizable design that relies on the binding of PIs to compete off a concatenated pseudoligand to generate the conformational change that leads to the RET change.

Components of PI Indicators

In some embodiments phosphoinositide indicators of the invention comprise a fusion protein comprising a pleckstrin homology (PH) domain of Akt (also known as protein kinase B) and a "pseudoligand" containing acidic amino acid residues, which is sandwiched between resonance energy transfer (RET) pairs, such as cyan and yellow mutants of GFP (a FRET pair). The pseudoligand portion of the indicator can be linked to either the N terminus or the C terminus the PH domain portion.

The pleckstrin homology (PH) domain of Akt binds specifically to two of the major PI3K products, $PIP_3$ and $PI(3,4)P_2$ (18, 19), and can be used in PI indicators of the invention to detect PI3K activity by binding to these products. Other phosphoinositide binding domains, such as phox homology (PX), FYVE domains, or PH domains from other proteins can be used to detect other products, such as $PI(4,5)P_2$, $PI(3)P$, etc. See (49).

Pseudoligand

The pseudoligand is a moiety (e.g., a peptide or small protein, or a compound) which binds to the same PH domain to which the respective PI binds; the binding sites on the PH domain to which the pseudoligand and the PI bind can be the same or different. The presence of the actual ligand (the PI) competes for binding with the pseudoligand or alter the binding with the pseudoligand. When the binding with the pseudoligand is changed, a conformational change is generated in the sensor containing the pseudoligand and the PH domain, which generates a RET response.

The amino acid sequence shown in SEQ ID NO:3 is a suitable pseudoligand for the PH domain of PKB/Akt that binds to $PIP_3$ and $PI(3,4)P_2$. Minor modifications of this amino acid sequence (e.g., VAEEDDDEEEDEDD; SEQ ID NO:17) can be made as long as the pseudoligand retains its ability to bind to the PH domain.

Subcellular Targeting Sequences

PI indicators of the invention can include a subcellular targeting sequence which can target an indicator to a subcellular domain such as a plasma membrane, a nuclear membrane, or other subcellular locations such as endoplasmic reticulum, Golgi apparatus, mitochondria, mitochondrial matrix, lysosomal lumen, or endosomal lumen. Many such targeting sequences are known in the art. Targeting sequences are known in the art. Examples include the plasma membrane targeting sequence shown in SEQ ID NO:4, the signal for geranylgeranylation (GerGer), a COOH-terminal CLLL from Rho; PalmPalm, an $NH_2$-terminal MLCCMRRTKQ (SEQ ID NO:6) from Gap43; MyrPalm, an $NH_2$-terminal MGCIKSKRKDNLNDDE (SEQ ID NO:7) from Lyn kinase; the nuclear localization signal sequence shown in SEQ ID NO:5, the mitochondrial localization sequence shown in SEQ ID NO:8, and the mitochondrial matrix targeting signal shown in SEQ ID NO:9.

Targeting sequences can be linked to PI indicators using, for example, a tetracysteine motif such as Cys Cys Xaa Xaa Cys Cys (SEQ ID NO:10). Targeting sequences can be linked at either the N- or C-terminus of a PI indicator (or a polypeptide portion of the PI indicator) or at intermediate points in the indicator.

Resonance Energy Transfer Pairs (Donor and Acceptor Moieties)

A resonance energy transfer pair (RET pair) contains a donor moiety and an acceptor moiety. As used here, a "donor moiety" is a fluorophore or a luminescent moiety. The absorption spectrum of the "acceptor moiety" overlaps the emission spectrum of the donor moiety. The acceptor moiety does not need to be fluorescent and can be a fluorophore, chromophore, or quencher. In some embodiments both the donor and acceptor moieties are fluorescent proteins. In other embodiments both the donor and acceptor moieties are luminescent moieties. In yet other embodiments, either one of the donor or acceptor moieties can be a fluorescent protein while the other moiety is a luminescent moiety. In other embodiments, the acceptor moiety is a "quencher moiety."

When both the donor and acceptor moieties are fluorophores, resonance energy transfer is detected as "fluorescence resonance energy transfer" (FRET). If a luminescent moiety is involved, resonance energy transfer is detected as "luminescent resonance energy transfer "(LRET). LRET includes "bioluminescent resonance energy transfer" (BRET; Boute et al., *Trends Pharmacol. Sci.* 23, 351-54, 2002; Ayoub et al., *J. Biol. Chem.* 277, 21522-28, 2002). Because excitation of the donor moiety does not require exogenous illumination in an LRET method, such methods are particularly useful in live tissue and animal imaging, because penetration of the excitation light is no longer a concern. LRET methods have a high contrast and high signal-to-noise ratio; 2) no photobleaching occurs; and 3) quantification is simplified because the acceptor moiety is not directly excited.

Suitable acceptor moieties include, for example, a coumarin, a xanthene, a fluorescein, a fluorescent protein, a circularly permuted fluorescent protein, a rhodol, a rhodamine, a resorufin, a cyanine, a difluoroboradiazaindacene, a phthalocyanine, an indigo, a benzoquinone, an anthraquinone, an azo compound, a nitro compound, an indoaniline, a diphenylmethane, a triphenylmethane, and a zwitterionic azopyridinium compound.

Suitable donor moieties include, but are not limited to, a coumarin, a xanthene, a rhodol, a rhodamine, a resorufin, a cyanine dye, a bimane, an acridine, an isoindole, a dansyl dye, an aminophthalic hydrazide, an aminophthalimide, an aminonaphthalimide, an aminobenzofuran, an aminoquinoline, a dicyanohydroquinone, a semiconductor fluorescent nanocrystal, a fluorescent protein, a circularly permuted fluorescent protein, and fluorescent lanthanide chelate.

Fluorescent Proteins

In some preferred embodiments either or both of the donor and acceptor moieties is a fluorescent protein. Suitable fluorescent proteins include green fluorescent proteins (GFP), red fluorescent proteins (RFP), yellow fluorescent proteins (YFP), and cyan fluorescent proteins (CFP). Useful fluorescent proteins also include mutants and spectral variants of these proteins which retain the ability to fluoresce.

RFPs include Discosoma RFPs, such Discosoma DsRed (SEQ ID NO: 11) or a mutant thereof which includes an Ile125Arg mutation, or a non-oligomerizing tandem DsRed containing, for example, two RFP monomers linked by a peptide linker. For example, a non-oligomerizing tandem RFP can contain two DsRed monomers or two mutant DsRed-1125R monomers linked by a peptide (having, for example, the amino acid sequence shown in SEQ ID NO:16).

Useful GFPs include an *Aequorea* GFP (e.g., SEQ ID NO:12), a *Renilla* GFP, a *Phialidium* GFP, and related fluorescent proteins for example, a cyan fluorescent protein (CFP), a yellow fluorescent protein (YFP), or a spectral variant of the CFP or YFP. CFP (cyan) and YFP (yellow) are color variants of GFP. CFP and YFP contain 6 and 4 mutations, respectively. They are Tyr66Try, Phe66Leu, Ser65Thr, Asn145Ile, Met153Thr, and Val163Ala in CFP and Ser65Gly, Val168Leu, Ser72Ala, and Thr203Tyr. Spectral variants include an enhanced GFP (EGFP; SEQ ID NO:13), an enhanced CFP (ECFP; SEQ ID NO:14), an enhanced YFP (EYFP; SEQ ID NO:15), and an EYFP with V68L and Q69K mutations. Other examples of fluorescent proteins comprising mutations are *Aequorea* GFP with one or more mutations at amino acid residues A206, L221 or F223 of SEQ ID NO:12 (e.g., mutations A206K, L221K, F223R, Q80R); mutations L221K and F223R of ECFP (SEQ ID NO:13), and EYFP-V68L/Q69K of SEQ ID NO:12. See also US 2004/0180378; U.S. Pat. Nos. 6,150,176; 6,124,128; 6,077,707; 6,066,476; 5,998,204; and 5,777,079; Chalfie et al., *Science* 263:802-805, 1994. The truncated ECFP shown in SEQ ID NO:18 (which can be encoded by the nucleotide sequence shown in SEQ ID NO: 19) is especially useful.

Other useful GFP-related fluorescent proteins include those having one or more folding mutations, and fragments of the proteins that are fluorescent, for example, an A. victoria GFP from which the two N-terminal amino acid residues have been removed. Several of these fluorescent proteins contain different aromatic amino acids within the central chromophore and fluoresce at a distinctly shorter wavelength than the wild type GFP species. For example, the engineered GFP proteins designated P4 and P4-3 contain, in addition to other mutations, the substitution Y66H; and the engineered GFP proteins designated W2 and W7 contain, in addition to other mutations, Y66W.

Folding mutations in *Aequorea* GFP-related fluorescent proteins improve the ability of the fluorescent proteins to fold at higher temperatures and to be more fluorescent when expressed in mammalian cells, but have little or no effect on the peak wavelengths of excitation and emission. If desired, these mutations can be combined with additional mutations that influence the spectral properties of GFP to produce proteins with altered spectral and folding properties, and, particularly, with mutations that reduce or eliminate the propensity of the fluorescent proteins to oligomerize. Folding mutations, with respect to SEQ ID NO:12, include the substitutions F64L, V68L, S72A, T44A, F99S, Y145F, N146I, M153T, M153A, V163A, 1167T, S175G, S205T, and N212K.

Luminescent Moieties

Luminescent moieties useful in a PI indicator include lanthanides, which can be in the form of a chelate, including a lanthanide complex containing the chelate (e.g, β-diketone chelates of cerium, praseodymium, neodymium, promethium, samarium, europium, gadolinium, terbium, dysprosium, holmium, erbium, thulium, or ytterbium). Lanthanide chelates are well known in the art. See Soini and Kojola, *Clin. Chem.* 29, 65, 1983; Hemmila et al., *Anal. Biochem.* 137, 335 1984; Lovgren et al., In: Collins & Hoh, eds., *Alternative Immunoassays*, Wiley, Chichester, U. K., p. 203, 1985; Hemmila, *Scand. J. Clin. Lab. Invest.* 48, 389, 1988; Mikola et al., *Bioconjugate Chem.* 6, 235, 1995; Peruski et al., *J. Immunol. Methods* 263, 35-41, 2002; U.S. Pat. No. 4,374,120; and U.S. Pat. No. 6,037,185. Suitable β-diketones are, for example, 2-naphthoyltrifluoroacetone (2-NTA), 1-naphthoyltrifluoroacetone (1-NTA), p-methoxybenzoyltrifluoroacetone (MO-BTA), p-fluorobenzoyltrifluoroacetone (F-BTA), benzoyltrifluoroacetone (BTA), furoyltrifluoroacetone (FTA), naphthoylfuroylmethane (NFM), dithenoylmethane (DTM), and dibenzoylmethane (DBM). See also US 20040146895.

Luminescent proteins include, but are not limited to, lux proteins (e.g., luxCDABE from *Vibrio fischerii*), luciferase proteins (e.g., firefly luciferase, *Gaussia* luciferase, *Pleuromamma* luciferase, and luciferase proteins of other beetles, Dinoflagellates (Gonylaulax; Pyrocystis), Annelids (Dipocardia), Molluscs (Lativai), and Crustacea (Vargula; Cypridina), and green fluorescent proteins of bioluminescent coelenterates (e.g., *Aequorea Victoria, Renilla mullerei, Renilla reniformis*; see Prendergast et al., *Biochemistry* 17, 3448-53, 1978; Ward et al., *Photochem. Photobiol.* 27, 389-96, 1978; Ward et al., *J. Biol. Chem.* 254, 781-88, 1979; Ward et al., *Photochem. Photobiol. Rev* 4, 1-57, 1979; Ward et al., *Biochemistry* 21, 4535-40, 1982). Many of these proteins are commercially available. Firefly luciferase is available from Sigma, St. Louis, Mo., and Boehringer Mannheim Biochemicals, Indianapolis, Ind. Recombinantly produced firefly luciferase is available from Promega Corporation, Madison, Wis. Jellyfish aequorin and luciferase from *Renilla* are commercially available from Sealite Sciences, Bogart, Ga.

The DNA sequences of the aequorin and other luciferases employed for preparation of some PI indicators of the invention can be derived from a variety of sources. For example, cDNA can be prepared from mRNA isolated from the species disclosed above. See Faust, et al., *Biochem.* 18, 1106-19, 1979; De Wet et al., *Proc. Natl. Acad. Sci. USA* 82, 7870-73, 1985.

Luciferase substrates (luciferins) are well known and include coelenterazine (available from Molecular Probes, Eugene, Oreg.) and ENDUREN™. These cell-permeable reagents can be directly administered to cells, as is known in the art. Luciferin compounds can be prepared according to the methods disclosed by Hori et al., *Biochemistry* 14, 2371-76, 1975; Hori et al., *Proc. Natl. Acad. Sci. USA* 74, 4285-87, 1977).

Dark Quenchers

In some embodiments the acceptor moiety is a quencher moiety, preferably a "dark quencher" (or "black hole quencher") as is known in the art. In this case, the change in conformation which occurs upon PI binding eliminates quenching, resulting in an increase in energy emission from the donor moiety. "Dark quenchers" themselves do not emit photons. Use of a "dark quencher" reduces or eliminates background fluorescence or luminescence which would otherwise occur as a result of energy transfer from the donor moiety. Suitable quencher moieties include dabcyl (4-(4'-dimethylaminophenylazo)-benzoic acid), QSY™-7 carboxylic acid, succinimidyl ester (N,N'-dimethyl-N,N'-diphenyl-4-((5-t-butoxycarbonylaminopentyl)aminocarbon yl) piperidinylsulfone-rhodamine (a diarylrhodamine derivative from Molecular Probes, Eugene, Oreg.). Suitable quencher moieties are disclosed, for example, in US 2005/0118619; US 20050112673; and US 20040146959.

Any suitable fluorophore may be used as the donor moiety provided its spectral properties are favorable for use with the chosen dark quencher. The donor moiety can be, for example, a Cy-dye, Texas Red, a Bodipy dye, or an Alexa dye. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, a fluorescein (e.g., fluorescein, tetrachlorofluorescein, hexachlorofluorescein), rhodamine, tetramethylrhodamine, or other like compound. Suitable fluorescent moieties for use with dark quenchers include xanthene dyes, such as fluorescein or rhodamine dyes, including 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl)aminonaphthalene-1-sulfonic acid (EDANS).

Other suitable fluorescent moieties include coumarins, such as 3-phenyl-7-isocyanatocoumarin; acridines, such as 9-isothiocyanatoacridin-e and acridine orange; N-(p-(2-benzoxazolyl)phenyl)maleimide; cyanines, such as indodicarbocyanine 3 (Cy3), indodicarbocyanine 5 (Cy5), indodicarbocyanine 5.5 (Cy5.5), 3-1-carboxy-pentyl)-3'-ethyl-5,5'-dimethyl-loxacarbocyanine (CyA); 1H, 5H, 1H, 15H-Xantheno[2,3,4-ij: 5,6,7-i'j']diquinol-izin-18-ium, 9-[2(or 4)-[[[6-[2,5-dioxo-1-pyrrolidinyl)oxy]-6-oxohexyl]amino] sulfonyl]-4(or 2)-sulfophenyl]-2,3,6,7,12,13,16,17-octahydro-inner salt (TR or Texas Red); BODIPY™ dyes; benzoxaazoles; stilbenes; pyrenes; and the like.

Nucleic Acid Molecules Encoding PI Indicators

In some embodiments, PI indicators contain only protein components. Such fusion proteins can be expressed recombinantly, and the invention provides nucleic acid molecules for this purpose. A nucleic acid molecule encoding a PI indicator can comprise any nucleotide sequence which encodes the amino acid sequence of the indicator. Nucleic acid molecules of the invention include single- and double-stranded DNA (including cDNA) and mRNA. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

In some embodiments the nucleic acid molecules are expression constructs which contain the necessary elements for the transcription and translation of an inserted coding sequence encoding a PI indicator. Expression constructs can be used as vectors for introducing PI indicators into cells. Methods which are well known to those skilled in the art can be used to construct expression vectors containing sequences encoding PI indicators and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., *Current Protocols in Molecular Biology*, John Wiley & Sons, New York, N.Y., 1989.

Expression vectors of the invention can be expressed in a variety of host cells. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems, particularly mammalian systems, including human systems. See WO 01/98340, which is incorporated herein by reference in its entirety. The choice of vector components and appropriate host cells is well within the capabilities of those skilled in the art.

Alternatively, protein or non-protein donor and/or acceptor moieties can be linked to the polypeptide by covalent attachment. There are a variety of methods known in the art which are useful for this purpose. For example, the attachment can be direct, via a functional group on the polypeptide (e.g., amino, carboxyl and sulthydryl groups) and a reactive group on the fluorophore. Free amino groups in the polypeptide can be reacted with fluorophores derivatized with isothiocyanate, maleic anhydride, N-hydroxysuccinimide, tetrafluorylphenyl and pentafluoryl esters. Free carboxyl groups in the polypeptide can be reacted with carbodiimides such as 1-ethyl-3-[dimethylaminopropyl]carbodiimide hydrochloride to create a reactive moiety that will react with an amine moiety on the donor or acceptor moiety. Sulfhydryl groups can be attached to donor or acceptor moieties modified with maleimide and iodoacetyl groups, although such linkages are more susceptible to reduction than linkages involving free amino groups. The polypeptide can also be linked indirectly via an intermediate linker or spacer group, using chemical groups such as those listed above.

It is also possible to produce PI indicators of the invention using chemical methods to synthesize the amino acid sequence of the polypeptide and, optionally, one or more fluorescent or luminescent proteins. Methods include direct peptide synthesis using solid-phase techniques (Merrifield, *J. Am. Chem. Soc.* 85, 2149-2154, 1963; Roberge et al., *Science* 269, 202-204, 1995). Protein synthesis can be performed using manual techniques or by automation. Automated synthesis can be achieved, for example, using Applied Biosystems 431A Peptide Synthesizer (Perkin Elmer). Optionally, fragments of polypeptide portions of PI indicators can be separately synthesized and combined using chemical methods to produce a full-length indicator molecule. See WO 01/98340.

Delivery of PI Indicators to Cells

PI indicators of the invention can be introduced into cells in vitro using reversible permeabilization techniques. See U.S. Pat. No. 6,127,177; U.S. Pat. No. 6,902,931; Russo et al., *Nature Biotechnology* 15, 278-82, March 1997; Santangelo et al., *Nucleic Acids Res.* 32, 1-9, Apr. 14, 2004.

If the PI indicator is a fusion protein, expression vectors comprising a PI indicator-encoding nucleotide sequence can be transfected into any cell in vitro in which it is desired to monitor PI3K activity or PI distribution. Any transfection method known in the art can be used, including, for example, including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Useful vectors and methods of delivering the vectors to cells in vivo are disclosed, for example, in U.S. Pat. No. 6,825,012; U.S. Pat. No. 6,878,549; U.S. Pat. No. 6,645,942; U.S. Pat. No. 6,692,737; U.S. Pat. No. 6,689,758; U.S. Pat. No. 6,669,935; and U.S. Pat. No. 6,821,957.

Methods of Detecting PI3K Activity

The invention provides various methods for detecting PI3K activity or PI distribution by detecting conformational changes in a PI indicator. Broadly, the methods involve detecting a change in resonance energy transfer of a PI indicator of the invention when the indicator binds to a PI. PI binding to the indicator induces a conformational change that changes resonance energy transfer from the donor moiety to the acceptor moiety.

A change in resonance energy transfer can readily be detected using methods well known in the art. See, e.g., US 2005/0118619; US 2002/0137115; US 2003/0165920; US 2003/0186229; US 2004/0137479; US 2005/0026234; US 2005/0054573; US 2005/0118619; U.S. Pat. No. 6,773,885; U.S. Pat. No. 6,803,201; U.S. Pat. No. 6,818,420; Ayoub et al., 2002; Boute et al., 2002; Domin et al., *Prog. Biomed. Optics and Imaging, Proc. SPIE, vol* 5139, 2003, pp 238-242; Evellin et al., *Methods Mol. biol.* 284, 259-70, 2004; Honda et al., *Proc. Natl. Acad. Sci. USA* 98, 437-42, Feb. 27, 2001; Honda et al., *Methods Mol. Biol.* 3, 27-44, 1005; Mongillo et al., *Cir. Res.* 95, 67-75, Jul. 9, 2004; Mongillo et al., *Methods Mol. Biol.* 307, 1-14, 2005; Nagai et al., *Proc. Natl. Acad. Sci. USA* 101, 10554-59, Jul. 20, 2004; Nikolaev et al., *J. Biol. Chem.* 279, 37215-18, 2004; Polit et al., *Eur. J. Biochem.* 270, 1413-23, 2003; Ponsioen et al., *EMBO Rep.* 5, 1176-80, 2004; Santangelo et al., *Nucl. Acids Res.* 32, 1-9, e-published Apr. 14, 2004; and Warrier et al., *Am. J. Physiol. Cell Phiol.* 289, C455-61, August 2005. Properties which can be detected as resonance energy transfer (RET) measurements include a molar extinction coefficient at an excitation wavelength, a quantum efficiency, an excitation spectrum, an emission spectrum, an excitation wavelength maximum, an emission wavelength maximum, a ratio of excitation amplitudes at two wavelengths, a ratio of emission amplitudes at two wavelengths, an excited state lifetime, anisotropy, a polarization of emitted light, resonance energy transfer, and a quenching of emission at a wavelength.

PI indicators of the invention can be used in cell-free systems, in isolated cells (for example, in primary cell culture or a cell line) or in cells in situ (e.g., in an isolated tissue sample, an isolated whole organ, or in a mammal). Subcellular distribution of PIs or changes in PI3K activity can be detected, for example, as described in the specific examples, below. Absolute PI levels can be detected by obtaining a RET measurement in the assay system and comparing it to a standard curve obtained in vitro.

Test compounds can be tested, for example, for the ability to inhibit PI3K activity (e.g., in drug-screening methods). Test compounds can be pharmacologic agents already known in the art to affect PI3K activity or can be compounds previously unknown to have such an activity. Compounds known to affect PI3K levels include, for example, wortmannin, LY294002, insulin, insulin-like growth factor 1 (IGF-1), PDGF, and PTEN inhibitors (e.g., bisperoxovanadium compounds and compounds disclosed in WO/2005/097119).

Test compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection.

All patents, patent applications, and references cited in this disclosure are expressly incorporated herein by reference. The above disclosure generally describes the present invention. A more complete understanding can be obtained by reference to the following specific examples, which describe the construction and testing of a PI indicator termed "InPAkt," which is a genetically targetable indicator for $PIP_3$ and $PI(3,4)P_2$. An amino acid sequence for InPAkt is shown in SEQ ID NO:20; this amino acid sequence can be encoded by the nucleotide sequence shown in SEQ ID NO:21. SEQ ID NO:20 does not include a subcellular targeting peptide sequence which, as disclosed above, can be attached at a variety of positions in the indicator. These examples are provided for purposes of illustration only and are not intended to limit the scope of the invention.

EXAMPLE 1

Methods

Reporter construction. The Akt/PKB PH domain (1-164) was created by PCR using full length human Akt (SEQ ID NO:1) as the template. The pseudoligand peptide sequence VAEEEDDEEEDEDD (SEQ ID NO:3) was inserted between the C-terminus of PH domain and N-terminus of improved versions of YFP, Citrine (16) or Venus (17). Double mutation R23A/R25A was incorporated by the QUICKCHANGE™ method (Stratagene) (FIG. 1). The constructs were first generated in pRSET B (Invitrogen) and subcloned into modified pcDNA3 (Invitrogen) behind a Kozako sequence for mammalian expression.

For plasma membrane targeting of InPAkt, the sequence KKKKKSKTKCVIM (SEQ ID NO:4) was used. For nuclear targeting, the nuclear localization signal (NLS) PKKKRKVEDA (SEQ ID NO:5) was attached to the C terminus of the Venus-containing construct.

Cell Culture. HEK293 and NIH3T3 cells were plated onto sterilized glass coverslips in 35-mm dishes and grown to 50-90% confluency in DMEM (10% FBS) at 37° C. with 5% $CO_2$. Cells were transfected with FUGENE®-6 (Roche), then serum starved for 24-36 h before imaging. Colocalization studies were performed by incubating transfected cells with Hoechst 33342 cell-permeable dyes (Molecular Probes) for staining nucleic acids.

Imaging. Cells were washed twice with Hanks' balanced salt solution buffer and maintained in the dark at room temperature with the addition of 50 ng/ml rat PDGF (Sigma), 100 ng/ml bovine insulin (Calbiochem), 50 nM IGF-1 (Sigma), or 20 µM LY294002 (Sigma) as described. Cells were imaged on a Zeiss Axiovert 200M microscope with a cooled CCD camera MicroMAX BFT512 (Roper Scientific, Trenton, N.J.) controlled by METAFLUOR 6.2 software (Universal Imaging, Downingtown, Pa.). Dual emission ratio imaging used a 420DF20 excitation filter, a 450DRLP dichroic mirror, and two emission filters (475DF40 for CFP and 535DF25 for YFP) alternated by a filter-changer Lambda 10-2 (Sutter Instruments, Novato, Calif.). Exposure time was 50-500 ms, and images were taken every 15-30 s. Fluorescence images were background-corrected by subtracting autofluorescence intensity of untransfected cells (or background with no cells) from the emission intensities of cells expressing fluorescent reporters. The ratios of yellow-to-cyan emissions were then calculated at different time points.

EXAMPLE 2

Development of a FRET Based Phosphoinositide Indicator

Design of the reporter. To measure the spatiotemporal dynamics of PIs in living cells, we employed a general molecular design in which binding of PIs in the "sensing unit" of the indicator can be translated into a change in the "reporting unit." A pair of fluorescent proteins that can undergo fluorescence resonance energy transfer (FRET), enhanced cyan fluorescent protein (ECFP) and improved versions of yellow fluorescent proteins (YFP) namely Citrine (16) or Venus (17), was employed as the reporting unit (FIGS. 1A, 1B). These two fluorophores can be genetically fused to a conformationally responsive element, the conformational change of which alters the relative distance and/or orientation of the two fluorophores and generates a change in the emission ratio. Recently many such reporters have been developed for measuring signaling molecules like $Ca^{2+}$, cGMP, cAMP, or signaling events such as protein phosphorylation (14, 15).

For the sensing component, we chose the pleckstrin homology (PH) domain of Akt that binds specifically to two of the major PI3K products, namely $PIP_3$ and $PI(3,4)P_2$ (18, 19). Crystal structure of this PH domain complexed to soluble inositol (1,3,4,5) tetrakisphosphate ($IP_4$) (20) shows that this motif forms a bowl like structure lined with basic residues into which the highly negatively charged headgroup is accommodated (FIG. 1A).

To convert the PI binding to a conformational change, we engineered a "pseudoligand" sequence to associate with the basic patch of amino acids responsible for PI binding. The pseudoligand is a series of acidic residues taken from nucelolin 1 which was shown to bind to PH domain of insulin receptor substrate 1 (21). In the absence of PIs, the pseudoligand is expected to interact with the basic residues in the PH domain. Once the natural ligand is accumulated, the pseudoligand is competed off, unblocking the PH domain and generating a conformational change (FIG. 1A). This conformational change is relayed to the FRET pairs, thus yielding a change in FRET as readout to monitor PI dynamics.

Cellular response. When this construct was expressed in NIH3T3 cells, the fluorescence was uniformly distributed throughout the cell (FIG. 1D, first image). A similar expression pattern was seen in HEK293 cells. To verify that our reporter was expressed in full length, lysates of HEK293 cells expressing this chimera were separated on SDS-PAGE and probed with anti-GFP antibody. This chimeric protein was of the expected molecular weight showing no proteolysis (FIG. 1C).

We next checked the ability of this chimera to detect changes in 3' PIs in response to agonist stimulation. NIH3T3 cells expressing this construct were serum-starved then stimulated with 50 ng/ml platelet-derived growth factor (PDGF). Stimulation of endogenous PDGF receptor (PDGFR) generated a FRET increase, resulting in an increase in the ratio of yellow-to-cyan emissions (FIGS. 1D, 1E), which was detectable within several seconds and reached a plateau of 25.4±3.7% [average±std] (n=9) within minutes ($t_{1/2}$=3.45±0.65 min). The FRET change occurred in the plasma membrane and was accompanied by the translocation of the reporter (FIG. 1D), reiterating that 3' PIs are mainly produced at the plasma membrane (22). To verify that the FRET response is caused by binding of $PIP_3$ and $PI(3,4)P_2$, we generated a variant of the reporter in which two critical residues in the PH domain, Arg23 and Arg25, which mainly contribute to D-3 phosphate recognition (20), are mutated. As shown in FIG. 1E, incorporating the mutations R23A/R25A into the chimeric protein completely abolished the FRET change.

To determine whether production of 3' PIs via PI3K activation is responsible for the FRET change, we pretreated cells with PI3K inhibitor LY294002 (20 μM). In the presence of the inhibitor, no emission ratio change was observed upon PDGF stimulation, but removal of the inhibitor recovered the response (FIG. 1F). In addition, this construct was shown to respond to microinjected dioctanoyl $PIP_3$ and its soluble headgroup $IP_4$ (FIG. 5), suggesting the FRET change is caused by ligand binding.

We next tested whether the FRET response was reversible. Addition of LY294002 resulted in a decrease in emission ratios (FIG. 1G), presumably due to the degradation of $PIP_3$ and $PI(3,4)P_2$ by lipid phosphatases. Similarly, another PI3K inhibitor, wortmannin, when added at 500 nM, could reverse the PDGF-stimulated response. Thus this reporter is useful in monitoring not only the production of PI3K products but also their degradation, and is designated as the indicator for Phosphoinositides based on Akt (InPAkt).

EXAMPLE 3

Differential Dynamics Stimulated by Different Growth Factors

Figure 2:
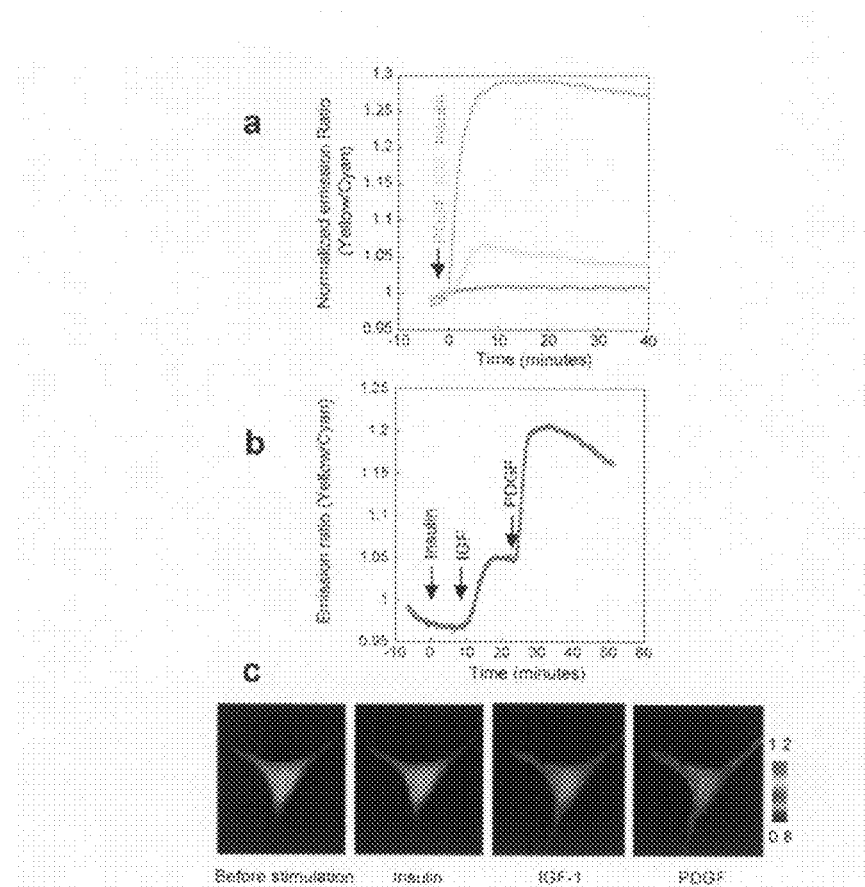
FIGS. 2A-C. Comparison of the cellular responses stimulated by various growth factors.

Although PI3K is a crucial regulatory component shared by various growth factor pathways, their differential coupling to PI3K isoforms (23), and distinct modes of negative regulation (24), could lead to significant difference in PI dynamics, thereby differentiating downstream signaling. To compare the accumulation of $PIP_3$ and $PI(3,4)P_2$ induced by the activation of different tyrosine kinase receptor pathways, we applied three different ligands, namely insulin, insulin-like growth factor 1 (IGF-1) and PDGF, to serum-starved NIH3T3 cells expressing InPAkt. As shown above, PDGF stimulation produced an acute response that reached a plateau of 25.4±3.7% ratio increase in 5-9 min ($t_{1/2}$=3.45±0.65 min) (FIG. 2A). In contrast, addition of 50 nM IGF-1 to activate insulin like growth factor receptor (IGF-IR) produced a more gradual response of 6.5±0.8% (n=5) in 10-12 min ($t_{1/2}$=5.4±0.4 min) (FIG. 2A). Finally, stimulation with 100 ng/ml insulin did not generate any discernable response possibly due to low copies of insulin receptor (IR) in NIH3T3 cells (25). Thus, the magnitude of the responses differed significantly in the increasing order of insulin<<IGF-1<PDGF.

To determine whether the mechanisms that account for the suboptimal responses stimulated by insulin or IGF-1 could affect the PDGF-stimulated responses, we applied three agonists sequentially with sufficient time intervals in between. First, the addition of insulin did not generate any appreciable change in the emission ratio, as shown above. When IGF-1 was added to activate IGF-IR, the emission ratios increased by 6.8±0.9% in 10-12 min ($t_{1/2}$=5.2±0.1 min) (n=3) and reached a plateau, indicating the production and degradation of $PIP_3$ and $PI(3,4)P_2$ reached an equilibrium. Lastly, when these fibroblasts were stimulated with PDGF, the emission ratio further increased by 14.6±1.4% in 6-7 min (n=4) ($t_{1/2}$=3.2±0.2 min) (FIGS. 2B, 2C), indicating the balance between PI3K and phosphatases shifted more toward production of PIs and subsequently reached a new equilibrium. Conversely, when we reversed the order of the ligand addition, with PDGF addition first, followed by IGF-1, PDGF stimulated a full response of 24.2+1.5% in 7-9 min (n=2) ($t_{1/2}$=3.9±0.2 min), which was not enhanced by the addition of IGF-1.

EXAMPLE 4

Phosphoinositide Dynamics within Subcellular Compartments

Figure 3:
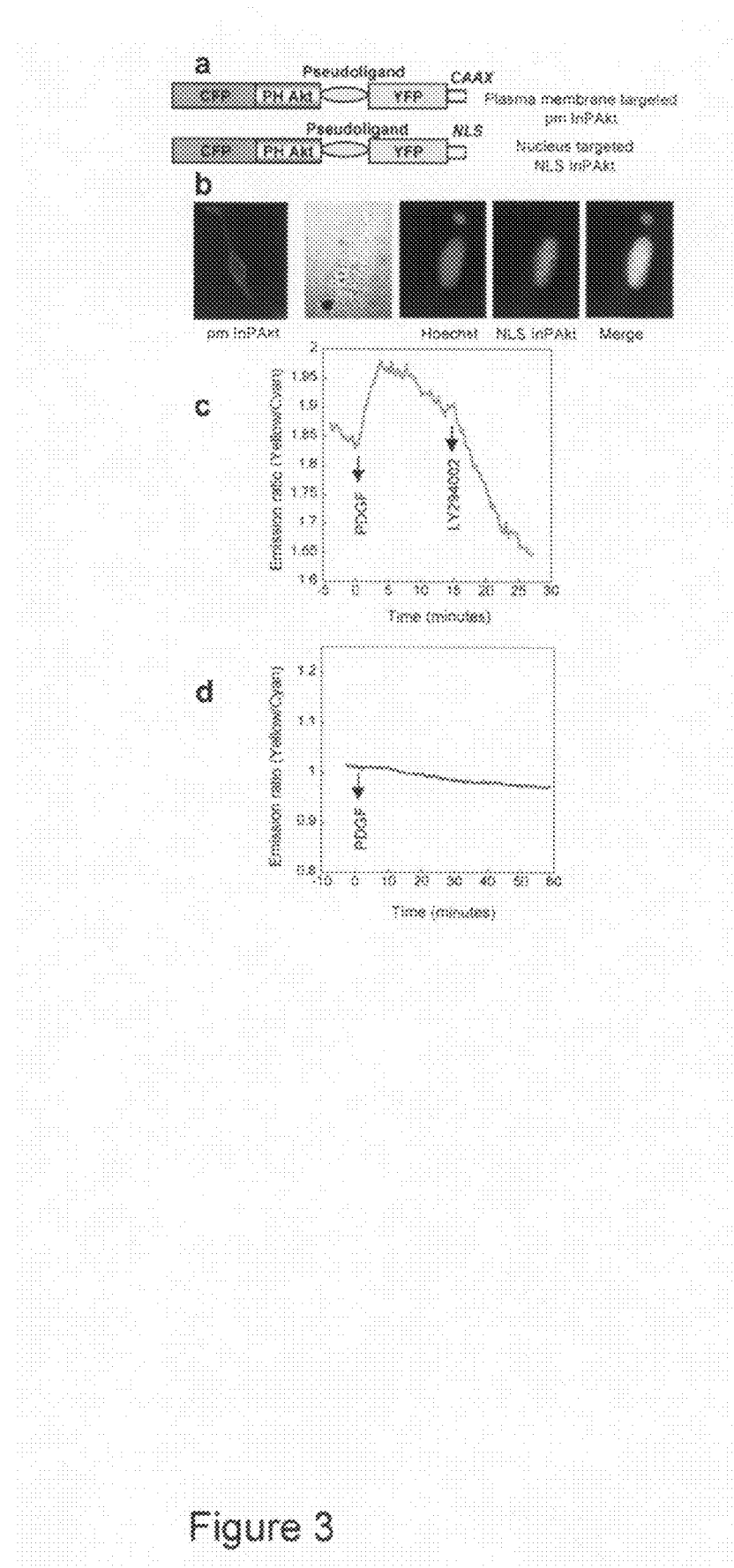
FIGS. 3A-D. Fusions of InPAkt targeted to various subcellular locations.
Figure 6:
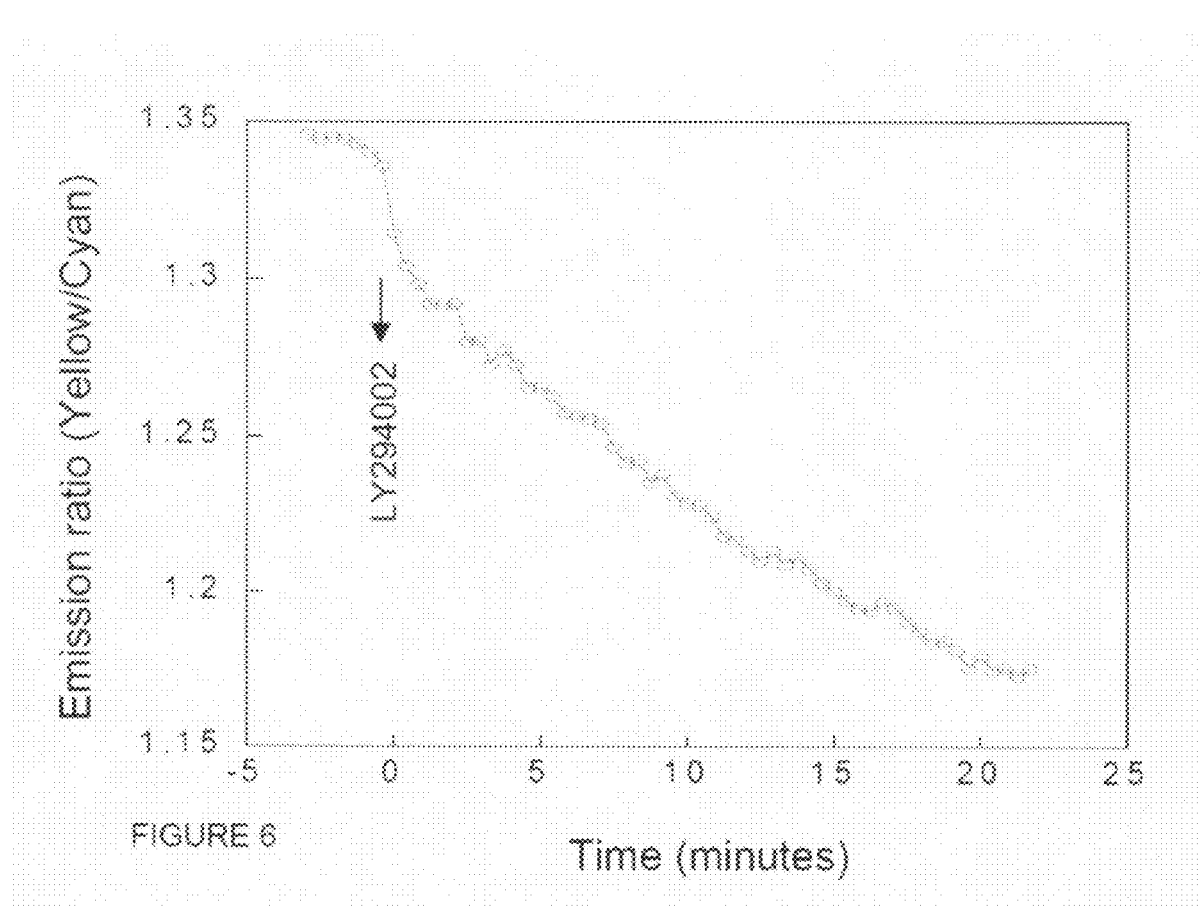
FIG. 6. Basal levels of PI(3,4)P$_2$ and PI(3,4,5)P$_3$ at the plasma membrane. Shown is a representative emission ratio time course of membrane-targeted InPAkt treated with phosphatidylinositol 3-kinase (PI3K) inhibitor LY294002 from two independent experiments. NIH 3T3 cells expressing plasma membrane-targeted InPAkt (pm InPAkt) were directly treated with PI3K inhibitor without prior stimulation with platelet-derived growth factor (PDGF). The decrease in emission ratio upon LY294002 addition confirmed the presence of high basal levels of PI(3,4)P$_2$ and PI(3,4,5)P$_3$ at the plasma membrane.

Plasma membrane. Taking advantage of the targetability of InPAkt, we constructed several fusions of InPAkt with various specific targeting motifs (FIG. 3A) to monitor $PIP_3$ dynamics at different subcellular locations inside cells. Attaching the plasma membrane-targeting sequence of small guanosine trisphosphatase K-ras4B to the C terminus of the InPAkt, localized the reporter to the plasma membrane (FIG. 3B). Upon PDGF stimulation, we observed a ratio change of 9.25±0.4% (n=4) in 6-8 min ($t_{1/2}$=3.9±0.7 min) (FIG. 3C). Compared to the responses from the untargeted reporter, (FIGS. 3C, 1G), the change in emission ratio was lesser for the membrane targeted InPAkt. Furthermore, upon addition of LY294002, we observed that the emission ratio decreased dramatically and reached below the initial ratio in the resting state. This data suggests the existence of basal levels of $PIP_3$ and $PI(3,4)P_2$ at the plasma membrane maintained by a critical balance between lipid kinase and phosphatase activities. Indeed, inhibition of PI3K led to a decrease in emission ratio in non-stimulated cells (FIG. 6).

Figure 8:
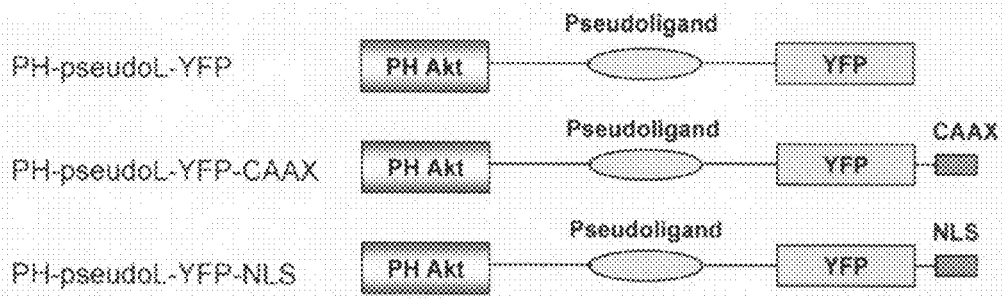
FIGS. 8A-C. Binding measurement of targeting sequence-tagged fusion constructs.
Figure 8:
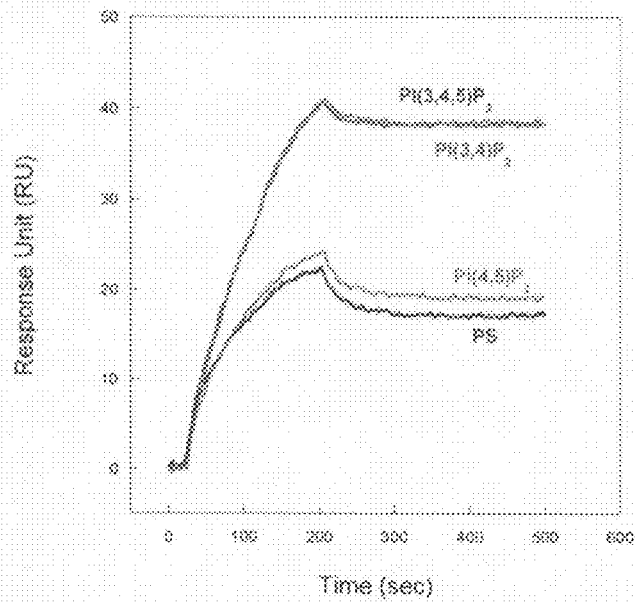

Nucleus. Although PI signaling research has been mainly focused on events at the plasma membrane, recent experimental evidence suggested presence of $PIP_3$ in the nucleus. For instance, it has been reported that PI3K translocates from cytoplasm to the nucleus (26), and presence of estrogen in cells containing a transmembrane intracellular estrogen receptor resulted in accumulation of $PIP_3$-binding PH domain in the nucleus (27). To directly visualize the presence and dynamics of $PIP_3$ and $PI(3,4)P_2$ in the nucleus, we targeted InPAkt to the nucleus by attaching a nuclear localization signal (NLS) (FIG. 3A), shown by colocalization with the nuclear staining with Hoechst dye (FIG. 3B). Upon stimulation with PDGF, the nuclear targeted InPAkt did not elicit any response in NIH3T3 cells (FIG. 3D). Furthermore, treatment with LY294002 did not produce any detectable change in FRET. On the other hand, microinjection of dioctanoyl $PIP_3$ and $IP_4$ into the nuclei of cells expressing the same construct generated emission ratio increases of 5.4±2.2% (n=3), and 9.1±0.42% (n=2), respectively (FIG. 7), indicating the nuclear localized InPAkt was functional. Furthermore, surface plasmon resonance (SPR) analysis showed attaching NLS did not significantly alter the binding affinity (FIG. 8). Hence, results from our reporter indicate that there may not be any appreciable amounts of accessible $PIP_3$ generated in the nucleus upon PDGF stimulation, in other words, these 3' PIs, if produced, may be accumulated in specific subnuclear compartments or complexed with other cellular components.

EXAMPLE 5

Simultaneous Imaging of Phosphoinositide Dynamics and Akt Phosphorylation

Increasing evidence has suggested that Akt, an immediate downstream effector of 3' PIs, is active within the nucleus (8). In the absence of accessible $PIP_3$ and $PI(3,4)P_2$ in the nucleus, how is nuclear Akt activity generated and maintained? It has been suggested that Akt gets activated at the plasma membrane by upregulated $PIP_3$ and subsequently translocates to the cytosol and at a later time point, to the nucleus (28). To directly assess the signal propagation from the plasma membrane to the nucleus, we used two different FRET reporters: InPAkt to monitor the production and degradation of PIP3 and $PI(3,4)P_2$ at the membrane; a nuclear targeted B kinase activity reporter (BKAR) to monitor Akt activity in the nucleus.

Briefly, BKAR is a genetically encoded fluorescent reporter (29) that monitors Akt activity. BKAR is comprised of ECFP and Citrine connected by a phosphoamino acid-binding domain (PBD) and an Akt specific substrate sequence, where phosphorylation of the substrate and its subsequent binding to PBD lead to a change in FRET, resulting in an increase in the ratio of cyan to yellow emissions. We previously reported that 3' PI production precedes Akt-mediated phosphorylation in the cytosol (29). To further examine the correlation between the PI dynamics at the membrane and Akt action in the nucleus with higher spatiotemporal resolution, we fused a NLS sequence to the C-terminus of BKAR (FIG. 4A) to target it to the nucleus (FIG. 4B), thereby achieving specific visualization of nuclear Akt activity. In addition, we used a plasma membrane targeted InPAkt to eliminate the possibility of probe translocation being a limiting step in kinetic measurement. When these two reporters were co-expressed, the spatial separation of the fluorescent signals allowed for simultaneous imaging of two closely coupled signaling events.

Figure 4:
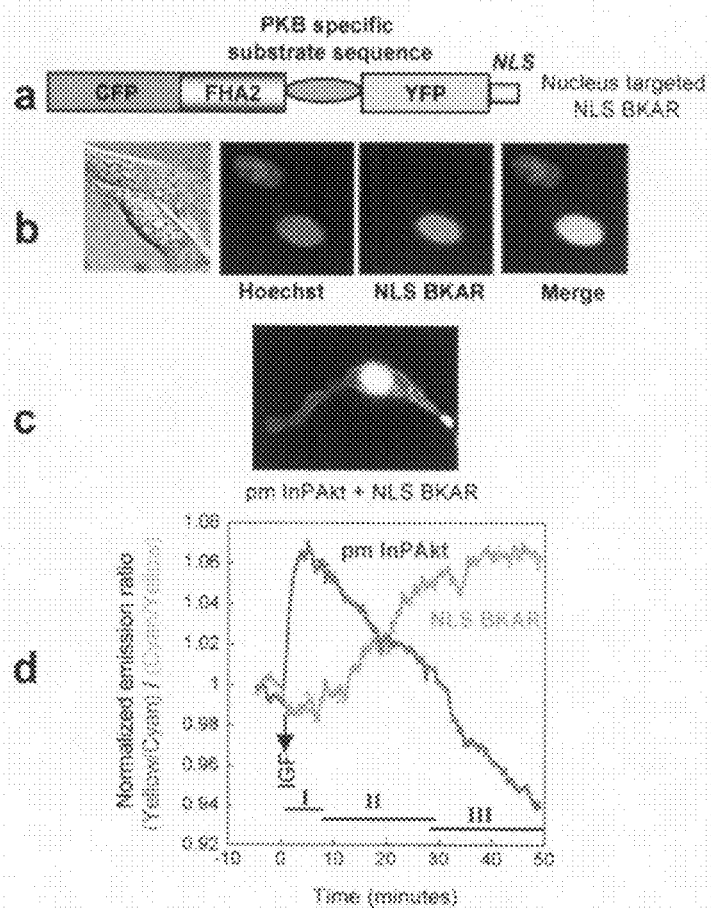
FIGS. 4A-D. Simultaneous imaging of plasma membrane targeted InPAkt (pm InPAkt) and nuclear targeted BKAR (NLS BKAR).

Following the aforementioned plan, we expressed both reporters in HEK293 cells (FIG. 4C). Upon IGF-1 treatment, we observed an immediate InPAkt response ($t_{1/2}$=3.4±0.7 min) (n=4) at the plasma membrane. However, in the same time frame (phase I in FIG. 4D), the emission ratio of BKAR in the nucleus remained unchanged, suggesting the signal propagation from the membrane to nucleus does not occur instantaneously. After the response of InPAkt reached a peak, the emission ratio began to decrease gradually, depicting the ongoing turnover of $PIP_3$ and $PI(3,4)P_2$. Notably, within this time frame (phase II), the cyan-to-yellow emission ratio of BKAR in the nucleus began to increase gradually. The delay of 5-8 minutes can be correlated with the time frame of the departure of Akt from the plasma membrane, its translocation into the nucleus (30) and subsequent phosphorylation of BKAR. The nuclear Akt activity continued to increase even after the level of $PIP_3$ and $PI(3,4)P_2$ was below the starting point (phase III), indicating continuing accumulation of active Akt in the nucleus, and reached a plateau in 35-40 minutes. This time course is similar to those recorded from cells expressing nuclear targeted BKAR alone, indicating expression of InPAkt does not sequester 3' PIs or affect endogenous Akt activity. Similar results were obtained in NIH3T3 cells stimulated by PDGF.

EXAMPLE 6

Responses of InPAkt at the Plasma Membrane

The responses from the plasma membrane-targeted InPAkt upon activation or inhibition of PI3K indicated the presence of basal levels of $PIP_3$ and $PI(3,4)P_2$ at the plasma membrane. Thus, some of the reporter molecules were pre-saturated with PIs and activation of PI3K generated a moderate increase, yet subsequent PI3K inhibition allowed phosphatases to act on both stimulated and basal PIs, leading to a larger decrease. The basal levels of these 3' PIs may be involved in constitutively activating the plasma membrane-targeted Akt (m/pAkt). In fact, it was shown that m/pAkt was still subject to inhibition by PI3K inhibitors (28), supporting our finding that the basal levels of $PIP_3$ and $PI(3,4)P_2$ are maintained by balanced activities of PI3K and phosphatases.

We observed distinct patterns of PI dynamics in response to activation of three different receptor tyrosine kinases (RTK), namely IR, IGF-IR and PDGFR in NIH3T3 cells, where PDGFR activation produces the largest response with fastest kinetics, consistent with data obtained using radioactive labeling (36). On the other hand, insulin induced a larger and more sustained response from PI3K activation than PDGF in 3T3 L1 adipocytes (37), one of the most insulin responsive cells expressing high levels of insulin receptors. However, the observed difference in responses stimulated by various growth factors cannot be accounted for solely by the difference in the total receptor numbers, as the numbers of PDGFR and IGF-IR per cell were similar [$1-2\times10^5$] (25, 38). Instead, the different dynamics may result from differential coupling of the activated receptors to PI3K, involving, for instance, PI3K isoform specific activation by different receptor signaling pathways (23), or their regulation of lipid phosphatases (39, 40). Furthermore, as a distinct mode of negative regulation, the p85 regulatory subunit of PI3K was shown to translocate to discrete foci after the initial production of 3' PI, in response to IGF-1, but not to PDGF signaling (24). Our results from sequential activation of receptors suggested the mechanisms responsible for the suboptimal IGF-1 response do not affect the subsequent PDGF signaling, at least at the PI level. Thus differential regulation by shared negative regulators such as lipid phosphatases either does not account for the suboptimal IGF-1 response or can be counteracted by PDGF stimulation.

EXAMPLE 7

Signal Propagation from the Plasma Membrane to Nucleus

InPAkt targeted to the nucleus did not show any detectable response in NIH3T3 cells stimulated by PDGF or HEK293 cells stimulated by IGF-1, suggesting no substantial amounts of accessible $PIP_3$ and $PI(3,4)P_2$ are accumulated in the nucleus under these conditions. Tanaka at al, using radiolabeling and cell fractionation, showed that nuclear fraction of PDGF-treated NIH3T3 cells contain only a small amount of PIP3 (41). While it is possible that small amounts of $PIP_3$ and $PI(3,4)P_2$ are present yet below the detection limit of InPAkt, it is also plausible that these 3' PI are accumulated in subnuclear compartment or form complexes with other components, in that InPAkt detects free accessible $PIP_3$ and $PI(3,4)P_2$ compared to total $PIP_3$ measured by Tanaka et al. Further experiments are needed to examine specific subnuclear compartments.

Upon growth factor stimulation, Akt gets activated at the plasma membrane and appears to maintain its activity during migration into the nucleus, rather than being activated by nuclear PI in situ. Using the plasma membrane-targeted PI indicator (InPAkt) and nuclear localized Akt activity reporter (BKAR), we show that Akt activity is gradually accumulated in the nucleus and sustained over 30-50 min, despite an immediate and transient production of $PIP_3$ and $PI(3,4)P_2$ at the plasma membrane. This observation is consistent with IGF-1 induced nuclear translocation of Akt1 over a 30 min period (28) and increased nuclear Akt activity detected by in vitro kinase assay (30, 42). The fact that this accumulation occurs in the presence of high levels of $PIP_3$ and $PI(3,4)P_2$ at the plasma membrane (phase II in FIG. 4d) suggests that a pool of activated Akt is able to detach from the plasma membrane and translocate into nucleus. It is speculated that the membrane associated Akt may undergo a conformational change following activation, reducing its membrane affinity and facilitating its dissociation from the membrane. Supporting this theory, it was shown that the association between PH domain of Akt and the plasma membrane was more sustained than the full length Akt (30). Furthermore, Akt remains active during nuclear translocation and thereafter, presumably by maintaining its phosphorylation at T308 and S473. Taken together, although lipid phosphatases are involved in maintaining the basal levels of 3' PIs and in shaping the stimulated transient response of the lipid second messenger, protein phosphatase activities are kept low to allow Akt mediated phosphorylation to sustain in the nucleus for 30-50 min or longer.

REFERENCES

1. Martin, T. F. (1998) *Annu. Rev. Cell Dev. Biol.* 14, 231-264.
2. Toker, A. (2002) *Cell Mol. Life. Sci.* 59, 761-779.
3. Fruman, D. A., Meyers, R. E. & Cantley, L. C. (1998) *Ann. Rev. Biochem.* 67, 481-507.
4. Maehama, T., Taylor, G. S. & Dixon, J. E. (2001) *Annu. Rev. Biochem.* 70, 247-279.
5. Krystal, G. (2000) *Semin. Immunol.* 12, 397-403.
6. Hanada, M., Feng, J. & Hemmings, B. A. (2004) *Biochim. Biophys. Acta* 1697, 3-16.
7. Scheid, M. P. & Woodgett, J. R. (2003) *FEBS Lett.* 546, 108-112.
8. Brazil, D. P., Yang, Z. Z. & Hemmings, B. A. (2004) *Trends Biochem. Sci.* 29, 233-242.
9. Lemmon, M. A. & Ferguson, K. M. (2001) *Biochem. Soc. Trans.* 29, 377-384.
10. Gray, A., Van Der, K. J. & Downes, C. P. (1999) *Biochem. J.* 344 Pt 3, 929-936.
11. Oatey, P. B., Venkateswarlu, K., Williams, A. G., Fletcher, L. M., Foulstone, E. J., Cullen, P. J. & Tavare, J. M. (1999) *Biochem. J.* 344 Pt 2, 511-518.
12. Stauffer, T. P., Ahn, S. & Meyer, T. (1998) *Curr. Biol.* 8, 343-346.
13. Varnai, P. & Balla, T. (1998) *J. Cell Biol.* 143, 501-510.
14. Miyawaki, A. (2003) *Developmental Cell* 4, 295-305.
15. Zhang, J., Campbell, R. E., Ting, A. Y. & Tsien, R. Y. (2002) *Nat. Rev. Mol. Cell. Biol.* 3, 906-918.
16. Griesbeck, O., Baird, G. S., Campbell, R. E., Zacharias, D. A. & Tsien, R. Y. (2001) *J. Biol. Chem.* 276, 29188-29194.
17. Nagai, T., Ibata, K., Park, E. S., Kubota, M., Mikoshiba, K. & Miyawaki, A. (2002) *Nat. Biotechnol.* 20, 87-90.
18. James, S. R., Downes, C. P., Gigg, R., Grove, S. J., Holmes, A. B. & Alessi, D. R. (1996) *Biochem. J.* 315 (Pt 3), 709-713.
19. Frech, M., Andjelkovic, M., Ingley, E., Reddy, K. K., Falck, J. R. & Hemmings, B. A. (1997) *J. Biol. Chem.* 272, 8474-8481.
20. Thomas, C. C., Deak, M., Alessi, D. R. & van Aalten, D. M. (2002) *Curr. Biol.* 12, 1256-1262.
21. Burks, D. J., Wang, J., Towery, H., Ishibashi, O., Lowe, D., Riedel, H. & White, M. F. (1998) *J. Biol. Chem.* 273, 31061-31067.
22. Czech, M. P. (2003) *Annu. Rev. Physiol* 65, 791-815.
23. Hooshmand-Rad, R., Hajkova, L., Klint, P., Karlsson, R., Vanhaesebroeck, B., Claesson-Welsh, L. & Heldin, C. H. (2000) *J. Cell Sci.* 113 Pt 2, 207-214.
24. Luo, J., Field, S. J., Lee, J. Y., Engelman, J. A. & Cantley, L. C. (2005) *J. Cell Biol.* in press
25. Hofmann, C., Goldfine, I. D. & Whittaker, J. (1989) *J. Biol. Chem.* 264, 8606-8611.
26. Neri, L. M., Borgatti, P., Capitani, S. & Martelli, A. M. (2002) *Biochim. Biophys. Acta* 1584, 73-80.
27. Revankar, C. M., Cimino, D. F., Sklar, L. A., Arterburn, J. B. & Prossnitz, E. R. (2005) *Science* 307, 1625-1630.
28. Andjelkovic, M., Alessi, D. R., Meier, R., Fernandez, A., Lamb, N. J., Frech, M., Cron, P., Cohen, P., Lucocq, J. M. & Hemmings, B. A. (1997) *J. Biol. Chem.* 272, 31515-31524.
29. Kunkel, M. T., Ni, Q., Tsien, R. Y., Zhang, J. & Newton, A. C. (2005) *J. Biol. Chem.* 280, 5581-5587.
30. Astoul, E., Watton, S. & Cantrell, D. (1999) *J. Cell Biol.* 145, 1511-1520.

31. Chen, R., Kang, V. H., Chen, J., Shope, J. C., Torabinejad, J., DeWald, D. B. & Prestwich, G. D. (2002) *J. Histochem. Cytochem.* 50, 697-708.
32. Violin, J. D., Zhang, J., Tsien, R. Y. & Newton, A. C. (2003) *J. Cell Biol.* 161, 899-909.
33. van der Wal, J., Habets, R., Varnai, P., Balla, T. & Jalink, K. (2001) *J. Biol. Chem.* 276, 15337-15344.
34. Sato, M., Ueda, Y., Takagi, T. & Umezawa, Y. (2003) *Nature Cell Biology* 5, 1016-1022.
35. Cicchetti, G., Biernacki, M., Farquharson, J. & Allen, P. G. (2004) *Biochemistry* 43, 1939-1949.
36. Jackson, T. R., Stephens, L. R. & Hawkins, P. T. (1992) *J. Biol. Chem.* 267, 16627-16636.
37. Tengholm, A. & Meyer, T. (2002) *Curr. Biol.* 12, 1871-1876.
38. Cohen, B. D., Goldstein, D. J., Rutledge, L., Vass, W. C., Lowy, D. R., Schlegel, R. & Schiller, J. T. (1993) *J. Virol.* 67, 5303-5311.
39. Ishihara, H., Sasaoka, T., Ishiki, M., Wada, T., Hori, H., Kagawa, S. & Kobayashi, M. (2002) *Mol. Endocrinol.* 16, 2371-2381.
40. Pesesse, X., Dewaste, V., De Smedt, F., Laffargue, M., Giuriato, S., Moreau, C., Payrastre, B. & Erneux, C. (2001) *J. Biol. Chem.* 276, 28348-28355.
41. Tanaka, K., Horiguchi, K., Yoshida, T., Takeda, M., Fujisawa, H., Takeuchi, K., Umeda, M., Kato, S., Ihara, S., Nagata, S. et al. (1999) *J. Biol. Chem.* 274, 3919-3922.
42. Borgatti, P., Martelli, A. M., Bellacosa, A., Casto, R., Massari, L., Capitani, S. & Neri, L. M. (2000) *FEBS Lett.* 477, 27-32.
43. DiPilato, L. M., Cheng, X. & Zhang, J. (2004) *Proc. Natl. Acad. Sci. U.S.A* 101, 16513-16518.
44. Burgering, B M. and Coffer, P. J. (1995) Nature, vol. 376, pages 599-602.
45. Alessi et al., Curr. Biol. vol. 7, 261 (1997).
46. Stokoe et al. (1997) Science, vol. 277, pages 567-570.
47. Bellacosa et al. (1995) Int. J. Cancer 64, pages 280-285.
48. Cheng et al. (1996) Proc. Natl. Acad. Sci. U.S.A. vol. 93, 3636-3641.
49. Lemmon, Traffic. 2003 April; 4(4): 201-13

The invention claimed is:

1. A nucleic acid molecule encoding a phosphoinositol (PI) indicator comprising the amino acid sequence SEQ ID NO:20.

2. The nucleic acid molecule of claim 1 which comprises the nucleotide sequence SEQ ID NO:21.

3. An isolated cell which comprises the nucleic acid molecule of claim 1.

4. The cell of claim 3, wherein the nucleic acid molecule comprises the nucleotide sequence SEQ ID NO:21.

* * * * *

SEQUENCE LISTING

```
<160> NUMBER OF SEQ ID NOS: 21

<210> SEQ ID NO 1
<211> LENGTH: 438
<212> TYPE: DNA
<213> ORGANISM: Homo sapiens

<400> SEQUENCE: 1
atgcatatga gcgacgtagc cattgtgaag gagggctggc tgcacaaacg agggaatat      60 attaaaacct ggcggccacg ctacttcctc ctcaagaacg atggcacctt tattggctac    120
aaggaacggc tcaggatgt ggatcagcga gagtccccac tcaacaactt ctcagtggca    180
ctatgccagc tgatgaagac agagcggcca aggcccaaca cctttatcat ccgctgcctg    240
cagtggacca cagtcattga gcgcaccttc catgtggaaa cgcctgagga gcggaagaa    300 tgggccaccg ccattcagac tgtggccgat ggactcaaga ggcaggaaga agagacgatg    360
gacttccgat caggctcacc cagtgacaac tcaggggctg aagagatgga ggtgtccctg    420
gccaagccca agcaccgt                                                 438

<210> SEQ ID NO 2
<211> LENGTH: 146
<212> TYPE: PRT
<213> ORGANISM: Homo sapiens

<400> SEQUENCE: 2

Met His Met Ser Asp Val Ala Ile Val Lys Glu Gly Trp Leu His Lys
 1               5                  10                  15

Arg Gly Glu Tyr Ile Lys Thr Trp Arg Pro Arg Tyr Phe Leu Leu Lys
            20                  25                  30

Asn Asp Gly Thr Phe Ile Gly Tyr Lys Glu Arg Pro Gln Asp Val Asp
        35                  40                  45

Gln Arg Glu Ser Pro Leu Asn Asn Phe Ser Val Ala Leu Cys Gln Leu
    50                  55                  60

Met Lys Thr Glu Arg Pro Arg Pro Asn Thr Phe Ile Ile Arg Cys Leu
65                  70                  75                  80

Gln Trp Thr Thr Val Ile Glu Arg Thr Phe His Val Glu Thr Pro Glu
                85                  90                  95
```

```
Glu Arg Glu Glu Trp Ala Thr Ala Ile Gln Thr Val Ala Asp Gly Leu
            100                 105                 110
Lys Arg Gln Glu Glu Thr Met Asp Phe Arg Ser Gly Ser Pro Ser
        115                 120                 125
Asp Asn Ser Gly Ala Glu Met Glu Val Ser Leu Ala Lys Pro Lys
    130                 135                 140
His Arg
145

<210> SEQ ID NO 3
<211> LENGTH: 14
<212> TYPE: PRT
<213> ORGANISM: Artificial Sequence
<220> FEATURE:
<223> OTHER INFORMATION: pseudoligand

<400> SEQUENCE: 3

Val Ala Glu Glu Glu Asp Asp Glu Glu Asp Glu Asp Asp
1               5                   10

<210> SEQ ID NO 4
<211> LENGTH: 13
<212> TYPE: PRT
<213> ORGANISM: Homo sapiens

<400> SEQUENCE: 4

Lys Lys Lys Lys Lys Ser Lys Thr Lys Cys Val Ile Met
1               5                   10

<210> SEQ ID NO 5
<211> LENGTH: 10
<212> TYPE: PRT
<213> ORGANISM: Homo sapiens

<400> SEQUENCE: 5

Pro Lys Lys Lys Arg Lys Val Glu Asp Ala
1               5                   10

<210> SEQ ID NO 6
<211> LENGTH: 10
<212> TYPE: PRT
<213> ORGANISM: Homo sapiens

<400> SEQUENCE: 6

Met Leu Cys Cys Met Arg Arg Thr Lys Gln
1               5                   10

<210> SEQ ID NO 7
<211> LENGTH: 16
<212> TYPE: PRT
<213> ORGANISM: Homo sapiens

<400> SEQUENCE: 7

Met Gly Cys Ile Lys Ser Lys Arg Lys Asp Asn Leu Asn Asp Asp Glu
1               5                   10                  15

<210> SEQ ID NO 8
<211> LENGTH: 30
<212> TYPE: PRT
<213> ORGANISM: Homo sapiens

<400> SEQUENCE: 8

Met Ala Ile Gln Leu Arg Ser Leu Phe Pro Leu Ala Leu Pro Gly Met
1               5                   10                  15
```

```
Leu Ala Leu Leu Gly Trp Trp Trp Phe Phe Ser Arg Lys Lys
            20                  25                  30
```

<210> SEQ ID NO 9
<211> LENGTH: 16
<212> TYPE: PRT
<213> ORGANISM: Homo sapiens

<400> SEQUENCE: 9

```
Met Leu Ser Leu Arg Gly Ser Ile Arg Phe Phe Lys Arg Ser Gly Ile
 1               5                  10                  15
```

<210> SEQ ID NO 10
<211> LENGTH: 6
<212> TYPE: PRT
<213> ORGANISM: Artificial Sequence
<220> FEATURE:
<223> OTHER INFORMATION: tetracysteine motif
<220> FEATURE:
<221> NAME/KEY: VARIANT
<222> LOCATION: 3, 4
<223> OTHER INFORMATION: Xaa = Any Amino Acid
<220> FEATURE:
<221> NAME/KEY: VARIANT
<222> LOCATION: 3, 4
<223> OTHER INFORMATION: Xaa = Any Amino Acid
<220> FEATURE:
<221> NAME/KEY: VARIANT
<222> LOCATION: 3, 4
<223> OTHER INFORMATION: Xaa = Any Amino Acid

<400> SEQUENCE: 10

```
Cys Cys Xaa Xaa Cys Cys
 1               5
```

<210> SEQ ID NO 11
<211> LENGTH: 225
<212> TYPE: PRT
<213> ORGANISM: Discosoma sp.

<400> SEQUENCE: 11

```
Met Arg Ser Ser Lys Asn Val Ile Lys Glu Phe Met Arg Phe Lys Val
 1               5                  10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
            35                  40                  45

Thr Lys Gly Gly Pro Leu Pro Phe Ala Trp Asp Ile Leu Ser Pro Gln
        50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
            115                 120                 125

Phe Pro Ser Asp Gly Pro Val Met Gln Lys Lys Thr Met Gly Trp Glu
        130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175
```

-continued

```
Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
            195                 200                 205

Thr Ile Val Glu Gln Tyr Glu Arg Thr Glu Gly Arg His His Leu Phe
            210                 215                 220

Leu
225

<210> SEQ ID NO 12
<211> LENGTH: 238
<212> TYPE: PRT
<213> ORGANISM: Aequoria victoria

<400> SEQUENCE: 12

Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
     50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 13
<211> LENGTH: 239
<212> TYPE: PRT
<213> ORGANISM: Aequoria victoria

<400> SEQUENCE: 13

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
             20                  25                  30
```

-continued

```
Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 14
<211> LENGTH: 239
<212> TYPE: PRT
<213> ORGANISM: Aequoria victoria

<400> SEQUENCE: 14

Met Val Ser Lys Gly Glu Glu Leu Phe Thr Gly Val Val Pro Ile Leu
 1               5                  10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Leu Thr Trp Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175
```

```
Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 15
<211> LENGTH: 239
<212> TYPE: PRT
<213> ORGANISM: Aequoria victoria

<400> SEQUENCE: 15

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Lys Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
            195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 16
<211> LENGTH: 18
<212> TYPE: PRT
<213> ORGANISM: Artificial Sequence
<220> FEATURE:
<223> OTHER INFORMATION: peptide linker

<400> SEQUENCE: 16

Gly Ser Thr Ser Gly Ser Gly Lys Pro Gly Ser Gly Gln Gly Ser Thr
1               5                   10                  15

Lys Gly
```

-continued

<210> SEQ ID NO 17
<211> LENGTH: 14
<212> TYPE: PRT
<213> ORGANISM: Artificial Sequence
<220> FEATURE:
<223> OTHER INFORMATION: pseudoligand

<400> SEQUENCE: 17

Val Ala Glu Glu Asp Asp Asp Glu Glu Glu Asp Glu Asp Asp
 1               5                  10

<210> SEQ ID NO 18
<211> LENGTH: 228
<212> TYPE: PRT
<213> ORGANISM: Aequoria victoria

<400> SEQUENCE: 18

Met Val Ser Lys Gly Glu Glu Leu Phe Thr Gly Val Val Pro Ile Leu
 1               5                  10                  15

Val Glu Leu Asp Gly Asp Val Asn Gly His Arg Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala
225

<210> SEQ ID NO 19
<211> LENGTH: 684
<212> TYPE: DNA
<213> ORGANISM: Aequoria victoria

<400> SEQUENCE: 19
atggtgagca agggcgagga gctgttcacc ggggtggtgc ccatcctggt cgagctggac     60
ggcgacgtaa acggccacag gttcagcgtg tccggcgagg gcgagggcga tgccacctac    120
ggcaagctga ccctgaagtt catctgcacc accggcaagc tgcccgtgcc ctggcccacc    180

```
ctcgtgacca ccctgacctg gggcgtgcag tgcttcagcc gctaccccga ccacatgaag    240
cagcacgact tcttcaagtc cgccatgccc gaaggctacg tccaggagcg taccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacat cagccacaac gtctatatca ccgccgacaa gcagaagaac    480
ggcatcaagg cccacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgcc                                           684
```

<210> SEQ ID NO 20
<211> LENGTH: 691
<212> TYPE: PRT
<213> ORGANISM: Artificial Sequence
<220> FEATURE:
<223> OTHER INFORMATION: phosphoinositide indicator
<400> SEQUENCE: 20

```
Met Arg Gly Ser His His His His His His Gly Met Ala Ser Met Thr
 1               5                  10                  15

Gly Gly Gln Gln Met Gly Arg Asp Leu Tyr Asp Asp Asp Lys Asp
                20                  25                  30

Pro Met Val Ser Lys Gly Glu Glu Leu Phe Thr Gly Val Val Pro Ile
             35                  40                  45

Leu Val Glu Leu Asp Gly Asp Val Asn Gly His Arg Phe Ser Val Ser
         50                  55                  60

Gly Glu Gly Glu Gly Asp Ala Thr Tyr Gly Lys Leu Thr Leu Lys Phe
 65                  70                  75                  80

Ile Cys Thr Thr Gly Lys Leu Pro Val Pro Trp Pro Thr Leu Val Thr
                 85                  90                  95

Thr Leu Thr Trp Gly Val Gln Cys Phe Ser Arg Tyr Pro Asp His Ile
            100                 105                 110

Lys Gln His Asp Phe Phe Lys Ser Ala Met Pro Glu Gly Tyr Val Gln
        115                 120                 125

Glu Arg Thr Ile Phe Phe Lys Asp Asp Gly Asn Tyr Lys Thr Arg Ala
    130                 135                 140

Glu Val Lys Phe Glu Gly Asp Thr Leu Val Asn Arg Ile Glu Leu Lys
145                 150                 155                 160

Gly Ile Asp Phe Lys Glu Asp Gly Asn Ile Leu Gly His Lys Leu Glu
                165                 170                 175

Tyr Asn Tyr Ile Ser His Asn Val Tyr Ile Thr Ala Asp Lys Gln Lys
            180                 185                 190

Asn Gly Ile Lys Ala His Phe Lys Ile Arg His Asn Ile Glu Asp Gly
        195                 200                 205

Ser Val Gln Leu Ala Asp His Tyr Gln Gln Asn Thr Pro Ile Gly Asp
    210                 215                 220

Gly Pro Val Leu Leu Pro Asp Asn His Tyr Leu Ser Thr Gln Ser Ala
225                 230                 235                 240

Leu Ser Lys Asp Pro Asn Glu Lys Arg Asp His Met Val Leu Leu Glu
                245                 250                 255

Phe Val Thr Ala Ala Arg Met His Met Ser Asp Val Ala Ile Val Lys
            260                 265                 270
```

```
Glu Gly Trp Leu His Lys Arg Gly Glu Tyr Ile Lys Thr Trp Arg Pro
            275                 280                 285
Arg Tyr Phe Leu Leu Lys Asn Asp Gly Thr Phe Ile Gly Tyr Lys Glu
        290                 295                 300
Arg Pro Gln Asp Val Asp Gln Arg Glu Ala Pro Leu Asn Asn Phe Ser
305                 310                 315                 320
Val Ala Gln Cys Gln Leu Met Lys Thr Glu Arg Pro Arg Pro Asn Thr
                325                 330                 335
Phe Ile Ile Arg Cys Leu Gln Trp Thr Thr Val Ile Glu Arg Thr Phe
            340                 345                 350
His Val Glu Thr Pro Glu Glu Arg Glu Glu Trp Thr Thr Ala Ile Gln
        355                 360                 365
Thr Val Ala Asp Gly Leu Lys Lys Gln Glu Glu Glu Met Asp Phe
370                 375                 380
Arg Ser Gly Ser Pro Ser Asp Asn Ser Gly Ala Glu Glu Met Glu Val
385                 390                 395                 400
Ser Leu Ala Lys Pro Lys His Arg Val Thr Met Asn Glu Phe Glu Tyr
                405                 410                 415
Leu Lys Leu Leu Gly Lys Gly Thr Phe Gly Lys Val Ser Ala Gly Gly
            420                 425                 430
Ser Val Ala Glu Glu Asp Asp Glu Glu Asp Glu Asp Gly
        435                 440                 445
Gly Ser Glu Leu Met Val Ser Lys Gly Glu Glu Leu Phe Thr Gly Val
    450                 455                 460
Val Pro Ile Leu Val Glu Leu Asp Gly Asp Val Asn Gly His Lys Phe
465                 470                 475                 480
Ser Val Ser Gly Glu Gly Glu Gly Asp Ala Thr Tyr Gly Lys Leu Thr
                485                 490                 495
Leu Lys Phe Ile Cys Thr Thr Gly Lys Leu Pro Val Pro Trp Pro Thr
            500                 505                 510
Leu Val Thr Thr Phe Gly Tyr Gly Leu Met Cys Phe Ala Arg Tyr Pro
        515                 520                 525
Asp His Met Lys Gln His Asp Phe Phe Lys Ser Ala Met Pro Glu Gly
    530                 535                 540
Tyr Val Gln Glu Arg Thr Ile Phe Phe Lys Asp Asp Gly Asn Tyr Lys
545                 550                 555                 560
Thr Arg Ala Glu Val Lys Phe Glu Gly Asp Thr Leu Val Asn Arg Ile
                565                 570                 575
Glu Leu Lys Gly Ile Asp Phe Lys Glu Asp Gly Asn Ile Leu Gly His
            580                 585                 590
Lys Leu Glu Tyr Asn Tyr Asn Ser His Asn Val Tyr Ile Met Ala Asp
        595                 600                 605
Lys Gln Lys Asn Gly Ile Lys Val Asn Phe Lys Ile Arg His Asn Ile
    610                 615                 620
Glu Asp Gly Ser Val Gln Leu Ala Asp His Tyr Gln Gln Asn Thr Pro
625                 630                 635                 640
Ile Gly Asp Gly Pro Val Leu Leu Pro Asp Asn His Tyr Leu Ser His
                645                 650                 655
Gln Ser Ala Leu Ser Lys Asp Pro Asn Glu Lys Arg Asp His Met Val
            660                 665                 670
Leu Leu Glu Phe Val Thr Ala Ala Gly Ile Thr Leu Gly Met Asp Glu
        675                 680                 685
Leu Tyr Lys
    690
```

<210> SEQ ID NO 21
<211> LENGTH: 2082
<212> TYPE: DNA
<213> ORGANISM: Artificial Sequence
<220> FEATURE:
<223> OTHER INFORMATION: coding sequence for IP Indicator

<400> SEQUENCE: 21

| | | | | | |
|---|---|---|---|---|---|
| atgcggggtt | ctcatcatca | tcatcatcat | ggtatggcta | gcatgactgg | tggacagcaa | 60 |
| atgggtcggg | atctgtacga | cgatgacgat | aaggatccca | tggtgagcaa | gggcgaggag | 120 |
| ctgttcaccg | gggtggtgcc | catcctggtc | gagctggacg | gcgacgtaaa | cggccacagg | 180 |
| ttcagcgtgt | ccggcgaggg | cgagggcgat | gccacctacg | gcaagctgac | cctgaagttc | 240 |
| atctgcacca | ccggcaagct | gcccgtgccc | tggcccaccc | tcgtgaccac | cctgacctgg | 300 |
| ggcgtgcagt | gcttcagccg | ctaccccgac | cacatcaagc | agcacgactt | cttcaagtcc | 360 |
| gccatgcccg | aaggctacgt | ccaggagcgt | accatcttct | tcaaggacga | cggcaactac | 420 |
| aagacccgcg | ccgaggtgaa | gttcgagggc | gacaccctgg | tgaaccgcat | cgagctgaag | 480 |
| ggcatcgact | tcaaggagga | cggcaacatc | ctggggcaca | gctggagta | caactacatc | 540 |
| agccacaacg | tctatatcac | cgccgacaag | cagaagaacg | gcatcaaggc | ccacttcaag | 600 |
| atccgccaca | acatcgagga | cggcagcgtg | cagctcgccg | accactacca | gcagaacacc | 660 |
| cccatcggcg | acggccccgt | gctgctgccc | gacaaccact | acctgagcac | ccagtccgcc | 720 |
| ctgagcaaag | accccaacga | gaagcgcgat | cacatggtcc | tgctggagtt | cgtgaccgcc | 780 |
| gccccgcatgc | atatgagcga | cgtggctatt | gtgaaggagg | gttggctgca | caaacgaggg | 840 |
| gagtacatca | agacctggcg | ccacgctac | ttcctcctca | agaatgatgg | cacct tcatt | 900 |
| ggctacaagg | agcggccgca | ggatgtggac | caacgtgagg | ctcccctcaa | caacttctct | 960 |
| gtggcgcagt | gccagctgat | gaagacgagg | cggccccggc | ccaacacctt | catcatccgc | 1020 |
| tgcctgcagt | ggaccactgt | catcgaacgc | accttccatg | tggagactcc | tgaggagcgg | 1080 |
| gaggagtgga | caaccgccat | ccagactgtg | gctgacggcc | tcaagaagca | ggaggaggag | 1140 |
| gagatggact | ccggtcggg | ctcacccagt | gacaactcag | gggctgaaga | gatggaggtg | 1200 |
| tccctggcca | agcccaagca | ccgcgtgacc | atgaacgagt | ttgagtacct | gaagctgctg | 1260 |
| ggcaagggca | ctttcggcaa | ggtgtctgca | ggcggtagcg | tggctgagga | agaggatgac | 1320 |
| gaggaggaag | acgaggacga | tggcggcagc | gagctcatgg | tgagcaaggg | cgaggagctg | 1380 |
| ttcaccgggg | tggtgcccat | cctggtcgag | ctggacggcg | acgtaaacgg | ccacaagttc | 1440 |
| agcgtgtccg | gcgagggcga | gggcgatgcc | acttacggca | agctgaccct | gaagttcatc | 1500 |
| tgcaccaccg | gcaagctgcc | cgtgccctgg | cccaccctcg | tgaccacctt | cggctacggc | 1560 |
| ctgatgtgct | tcgcccgcta | ccccgaccac | atgaagcagc | acgacttctt | caagtccgcc | 1620 |
| atgcccgaag | gctacgtcca | ggagcgcacc | atcttcttca | aggacgacgg | caactacaag | 1680 |
| acccgcgccg | aggtgaagtt | cgagggcgac | accctggtga | accgcatcga | gctgaagggc | 1740 |
| atcgacttca | aggaggacgg | caacatcctg | gggcacaagc | tggagtacaa | ctacaacagc | 1800 |
| cacaatgtct | atatcatggc | cgacaagcag | aagaacggca | tcaaggtgaa | cttcaagatc | 1860 |
| cgccacaaca | tcgaggacgg | cagcgtgcag | ctcgccgacc | actaccagca | gaacaccccc | 1920 |
| atcggcgacg | gccccgtgct | gctgcccgac | aaccactacc | tgagccacca | gtccgccctg | 1980 |
| agcaaagacc | ccaacgagaa | gcgcgatcac | atggtcctgc | tggagttcgt | gaccgccgcc | 2040 |
| gggatcactc | tcggcatgga | cgagctgtac | aagtaagaat | tc | | 2082 |